United States Patent [19]
Llinas-Brunet et al.

[11] Patent Number: 6,143,715
[45] Date of Patent: Nov. 7, 2000

[54] HEPATITIS C INHIBITOR PEPTIDE ANALOGUES

[75] Inventors: Montse Llinas-Brunet; Murray D. Bailey, both of Pierrefonds; Teddy Halmos; Marc-André Poupart, both of Laval; Youla Tsantrizos, Saint-Laurent, all of Canada

[73] Assignee: Boehringer Ingelheim (Canada) Ltd., Laval, Canada

[21] Appl. No.: 09/131,433

[22] Filed: Aug. 10, 1998

Related U.S. Application Data

[60] Provisional application No. 60/055,247, Aug. 11, 1997.
[51] Int. Cl.$^7$ ............................... A61K 38/04; C07K 5/00
[52] U.S. Cl. .................... 514/2; 514/17; 514/18; 530/329; 530/330; 424/189.1
[58] Field of Search .................... 530/329–30; 514/2, 514/17–18; 424/189.1

[56] References Cited

U.S. PATENT DOCUMENTS

| | | |
|---|---|---|
| 4,691,007 | 9/1987 | Dutta et al. ............................ 530/331 |
| 5,633,388 | 5/1997 | Diana et al. . |
| 5,866,684 | 2/1999 | Attwood et al. ....................... 530/329 |

FOREIGN PATENT DOCUMENTS

| | | |
|---|---|---|
| WO 97/06804 | 2/1997 | WIPO . |
| WO 98/17679 | 5/1998 | WIPO . |
| WO98/22496 | 5/1998 | WIPO . |
| WO 98/46597 | 10/1998 | WIPO . |
| WO 98/46630 | 10/1998 | WIPO . |

OTHER PUBLICATIONS

Chu et al., Structure of Sch 68631: A new Hepatitis C Virus proteinase inhibitor from streptomyces sp., Tetrahedron Letters, 1996, vol. 37, pp. 7229–7232.

Matsumoto et al., 3D modeling of HCV protease and computer screening of its inhibitors, Antiviral Research, vol. 30, No. 1 p. A23 (abstract 19) 1996.

Steinkühler et al., Product inhibition of the Hepatitis C Virus NS3 protease, Biochemistry, vol. 37, pp. 8899–8905, 1968.

Ingallinella et al., Potent peptide inhibitors of human Hepatitis C Virus NS3 protease are obtained by optimizing the cleavage products, Biochemisty, vol. 37, pp. 8906–8914, 1998.

Mori, E.A., "The N–terminal region of NS3 serine protease of HCV is important to maintain its enzymatic integrity", Biochem. Biophys. Res. Comm., vol. 231, No. 3, Feb. 24, 1997, pp. 738–742.

Landro, E.A., "Mechanistic role of NS4A peptide cofactor with the truncated NS3 protease of HCV: elucidation of the NS4A stimulatory effect via kinetic mapping and inhibitor mapping", Biochemistry, vol. 36, No. 31, Aug. 5, 1997, pp. 9340–9348.

*Primary Examiner*—Bennett Celsa
*Attorney, Agent, or Firm*—Robert P. Raymond; Mary-Ellen M. Devlin; Alan R. Stempel

[57] ABSTRACT

Compound of formula (I) active against the Hepatitis C virus:

$$\text{(I)}$$

wherein B is an acyl derivative; a is 0 or 1; $R_6$, when present, is carboxy(lower)alkyl; b is 0 or 1; $R_5$, when present, is $C_{1-6}$ alkyl, or carboxy (lower)alkyl; Y is H or $C_{1-6}$ alkyl; $R_4$ is $C_{1-10}$ alkyl; $R_3$ is $C_{1-10}$ alkyl; W is —NH—CH($R_2$)—C(O)—, wherein $R_2$ is $C_{1-6}$ alkyl; $C_6$ or $C_{10}$ aryl; $C_{7-16}$ aralkyl; or carboxy (lower)alkyl; or W is a proline derivative; Q is a group of the formula —Z($R_1$)—C(O)—$R_{13}$, wherein Z is CH or N; $R_1$ is $C_{1-6}$ alkyl or $C_{1-6}$ alkenyl both optionally substituted with thio or halo,; and $R_{13}$ is an activated carbonyl substituent, or Q is a phosphonate group of the formula —CH($R_1$)—P(O)$R_{15}R_{16}$ wherein $R_{15}$ and $R_{16}$ are independently $C_{6-20}$ aryloxy; and $R_1$ is as defined above.

33 Claims, No Drawings

HEPATITIS C INHIBITOR PEPTIDE ANALOGUES

This application claims the benefit of U.S. Provisional Application Ser. No. 60/055,247, filed Aug. 11, 1997.

FIELD OF THE INVENTION

The present invention relates to compounds, compositions and methods for the treatment of hepatitis C virus (HCV) infection. In particular, the present invention provides novel peptides and analogues thereof, pharmaceutical compositions containing such peptides and methods for using these peptides in the treatment; of HCV infection.

BACKGROUND OF THE INVENTION

Hepatitis C virus (HCV) is the major etiological agent of post-transfusion and community-acquired non-A non-B hepatitis worldwide. It is estimated that over 100 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis. However, the Center for Disease Control does not presently recommend immunoglobulins; for this purpose.

The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy.

Therefore, a need exists for the development of effective antiviral agents for treatment of HCV infection that overcomes the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus. In this vein, patent application WO 97/06804 describes the (−) enantiomer of the nucleoside analogue cytosine-1,3-oxathiolane (also known as 3TC) as active against HCV. This compound, although reported as safe in previous clinical trials against HIV and HBV, has yet to be clinically proven active against HCV and its mechanism of action against the virus has yet to be reported.

Intense efforts to discover compounds which inhibit the NS3 protease or RNA helicase of HCV have led to the following disclosures:

U.S. Pat. No. 5,633,388 describes heterocyclic-substituted carboxamides and analogues as being active against HCV. These compounds are directed against the helicase activity of the NS3 protein of the virus but clinical tests have not yet been reported.

A phenanthrenequinone has been reported by Chu et al (Tet. Lett., (1996), 7229–7232) to have activity against the HCV NS3 protease in vitro. No further development on this compound has been reported.

A paper presented at the Ninth International Conference on Antiviral Research, Urabandai, Fukyshima, Japan (1996) (Antiviral Research, 30, 1, 1996; A23 (abstract 19)) reports thiazolidine derivatives to be inhibitory to the HCV protease.

Several studies have reported compounds inhibitory to other serine proteases, such as human leukocyte elastase. One family of these compounds is reported in WO 95/33764 (Hoechst Marion Roussel, 1995). The peptides disclosed in that application are morpholinylcarbonyl-benzoyl-peptide analogues that are structurally different from the peptides of the present invention.

WO 98/17679 from Vertex Pharmaceuticals Inc. discloses inhibitors of serine protease, particularly, Hepatitis C virus NS3 protease. These inhibitors are peptide analogues based on the NS5A/5B natural substrate that contain C-terminal aldehydes, α-ketoamides and fluorinated ketones.

Hoffman LaRoche has also reported hexapeptides that are proteinase inhibitors useful as antiviral agents for the treatment of HCV infection. These peptides contain an aldehyde or a boronic acid at the C-terminus.

Steinkühler et al. and Ingallinella et al. have published on NS4A-4B product inhibition (Biochemistry (1998), 37, 8899–8905 and 8906–8914). However, these peptides and analogues were published after the priority date of the present application.

One advantage of the present invention is that it provides peptides that are inhibitory to the NS3 protease of the hepatitis C virus.

SUMMARY OF THE INVENTION

We investigated peptides potentially inhibitory to the NS3 protease. The discovery that the N-terminal cleavage product (Ac-D-D-I-V-P-C-OH) of an analogue of a natural substrate of the NS3 protease was inhibitory led us to the peptide analogues of the invention.

Included in the scope of the invention are compounds of formula (I):

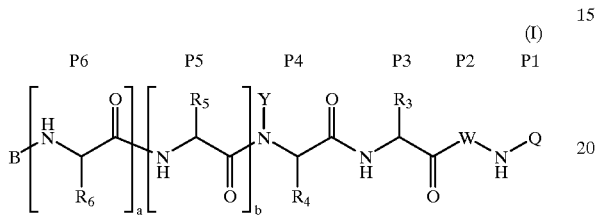

(I)

wherein B is an acyl derivative of formula $R_{11}$—C(O)— wherein $R_{11}$ is $C_{1-10}$ alkyl $C_{3-10}$ cycloalkyl optionally substituted with carboxyl; or $R_{11}$ is $C_6$ or $C_{10}$ aryl or $C_{7-16}$ aralkyl optionally substituted with a $C_{1-6}$ alkyl;

a is 0 or 1;

$R_6$, when present, is carboxy(lower)alkyl;

b is 0 or 1;

$R_5$, when present, is $C_{1-6}$ alkyl, or carboxy (lower) alkyl;

Y is H or $C_{1-6}$ alkyl;

$R_4$ is $C_{1-10}$ alkyl; cycloalkyl $C_{3-10}$;

$R_3$ is $C_{1-6}$ alkyl; cycloalkyl $C_{3-10}$;

W is a group of formula II:

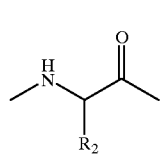

Formula II wherein $R_2$ is $C_{1-10}$ alkyl or $C_{3-7}$ cycloalkyl optionally substituted with carboxyl; $C_6$ or $C_{10}$ aryl; or $C_{7-16}$ aralkyl; or W is a group of formula II':

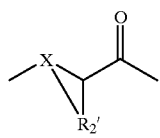

Formula II' wherein X is CH or N; and $R_2'$ is $C_{3-4}$ alkylene that joins X to form a 5- or 6-membered ring, said ring optionally substituted with OH; SH; $NH_2$; carboxyl; $R_{12}$, $OR_{12}$, $SR_{12}$, $NHR_{12}$ or $NR_{12}R_{12}'$ wherein $R_{12}$ and $R_{12}'$ are independently:

cyclic $C_{3-16}$ alkyl or acyclic $C_{1-16}$ alkyl or cyclic $C_{3-16}$ alkenyl or acyclic $C_{2-16}$ alkenyl, said alkyl or alkenyl optionally substituted with $NH_2$, OH, SH, halo, or carboxyl; said alkyl or alkenyl optionally containing at least one heteroatom selected independently from the group consisting of: O, S, and N; or $R_{12}$ and $R_{12}'$ are independently $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl; said aryl or aralkyl optionally containing at least one heteroatom selected independently from the group consisting of: O, S, and N;

said cyclic alkyl, cyclic alkenyl, aryl or aralkyl being optionally fused with a second 5-, 6- or 7-membered ring to form a cyclic system or heterocycle, said second ring being optionally substituted with $NH_2$, OH, SH, halo, carboxyl or carboxy(lower)alkyl; said second ring optionally containing at least one heteroatom selected independently from the group consisting of: O, S, and N;

Q is a group of the formula:

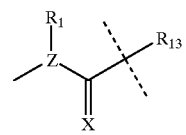

wherein Z is CH or N;

X is O or S;

$R_1$ is H, $C_{1-6}$ alkyl or $C_{1-6}$ alkenyl both optionally substituted with thio or halo; and when Z is CH, then $R_{13}$ is H; $CF_3$; $CF_2CF_3$; $CH_2$—$R_{14}$; CH (F)—$R_{14}$; $CF_2$—$R_{14}$; $NR_{14}R_{14}'$ S—$R_{14}$; or CO—NH—$R_{14}$ wherein $R_{14}$ and $R_{14}'$ are independently hydrogen, cyclic $C_{3-10}$ alkyl or acyclic $C_{1-10}$ alkyl or Cyclic $C_{3-10}$ alkenyl or acyclic $C_{2-10}$ alkenyl, said alkyl or alkenyl optionally substituted with $NH_2$, OH, SH, halo or carboxyl; said alkyl or alkenyl optionally containing at least one heteroatom selected independently from the group consisting of: O, S, and N; or $R_{14}$ and $R_{14}'$ are independently $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl or substituted with a further $C_{3-7}$ cycloalkyl, $C_6$ or $C_{10}$ aryl, or heterocycle; said aryl or aralkyl optionally containing at least one heteroatom selected independently from the group consisting of: O, S, and N;

said cyclic alkyl, cyclic alkenyl, aryl or aralkyl being optionally fused with a second 5-, 6-, or 7-membered ring to form a cyclic system or heterocycle, said second ring being optionally substituted with $NH_2$, OH, SH, halo, carboxyl or carboxy(lower)alkyl or substituted with a further $C_{3-7}$ cycloalkyl, $C_6$ or $C_{10}$ aryl, or heterocycle; said second ring optionally containing at least one heteroatom selected independently from the group consisting of: O, S, and N;

or $R_{14}$ and $R_{14}$, are independently $C_{1-4}$ alkyl which when joined together with N form a 3 to 6-membered nitrogen-containing ring which is optionally fused with a further $C_{3-7}$ cycloalkyl, $C_6$ or $C_{10}$ aryl or heterocycle;

with the proviso that when Z is CH, then $R_{13}$ is not an α-amino acid or an ester thereof;

when Z is N, then $R_{13}$ is H; carboxy; $C_{1-6}$ alkyl optionally substituted with carboxy; $CH_2$—$R_{14}$; $CHR_{14}R_{14}'$; CH(F)—$R_{14}$; O—$R_{14}$; $NR_{14}R_{14}'$ or S—$R_{14}$ wherein $R_{14}$ and $R_{14}'$ are as defined above; or Q is a phosphonate group of the formula:

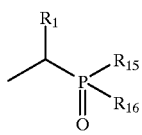

wherein $R_{15}$ and $R_{16}$ are independently $C_{6-20}$ aryloxy; and $R_1$ is as defined above.

Included within the scope of this invention is a pharmaceutical composition comprising an anti-hepatitis C virally effective amount of a compound of formula I, or a therapeutically acceptable salt or ester thereof, in admixture with a pharmaceutically acceptable carrier medium or auxiliary agent.

An important aspect of the invention involves a method of treating a hepatitis C viral infection in a mammal by administering to the mammal an anti-hepatitis C virally effective amount of the compound of formula I, or a therapeutically acceptable salt or ester thereof or a composition as described above.

Another important aspect involves a method of inhibiting the replication of hepatitis C virus by exposing the virus to a hepatitis C viral NS3 protease inhibiting amount of the compound of formula I, or a therapeutically acceptable salt or ester thereof or a composition as described above.

Still another aspect involves a method of treating a hepatitis C viral infection in a mammal by administering thereto an anti-hepatitis C virally effective amount of a combination of the compound of formula I, or a therapeutically acceptable salt or ester thereof, and an interferon. A pharmaceutical composition comprising the combination in admixture with a pharmaceutically acceptable carrier medium or auxiliary agent is also within the scope of this invention.

DETAILED DESCRIPTION OF THE INVENTION

As used herein, the following definitions apply unless otherwise noted:

With reference to the instances where (R) or (S) is used to designate the configuration of a radical, e.g. $R_4$ of the compound of formula I, the designation is done in the context of the compound and not in the context of the radical alone.

The natural amino acids, with exception of glycine, contain a chiral carbon atom. Unless otherwise specifically indicated, the compounds containing natural amino acids with the L-configuration are preferred. However, applicants contemplate that when specified, some amino acids of the formula I can be of either D- or L-configuration or can be mixtures of D- and L-isomers, including racemic mixtures.

The designation "P1, P2, P3 et." as used herein refer to the position of the amino acid residues starting from the C-terminus end of the peptide analogues and extending towards the N-terminus (i.e. P1 refers to position 1 from the C-terminus, P2: second position from the C-terminus, etc.) (see Berger A. & Schechter I., Transactions of the Royal Society London series, (1970), B257, 249–264).

The abbreviations for the α-amino acids are set forth in Table A.

TABLE A

| AMINO ACID | SYMBOL |
|---|---|
| Allylglycine | AlGly |
| Aminobutyric acid | Abu |
| Alanine | Ala |
| Aspartic acid | Asp |
| Cysteine | Cys |
| Cyclohexylalanine | Cha |
| Cyclohexylglycine (also named: 2-amino-2-cyclohexylacetic acid) | Chg |
| Glutamic acid | Glu |
| Isoleucine | Ile |
| Leucine | Leu |
| Norvaline | Nva |
| Phenylalanine | Phe |
| Pipecolic acid | Pip |
| Proline | Pro |
| 4(R)-Hydroxyproline | Hyp |
| 4(R)-Benzyloxyproline | Hyp(4-Bn) |
| Valine | Val |
| tert-Butylglycine | Tbg |

As used herein the term "aminobutyric acid" refers to a compound of formula:

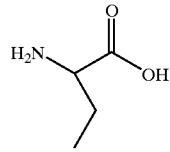

As used herein the term "allylglycine" refers to a compound of formula:

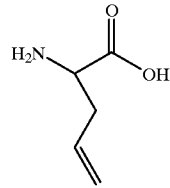

As used herein the term "tert-butylglycine" refers to a compound of formula:

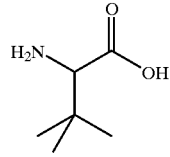

The term "residue" with reference to an amino acid or amino acid derivative means a radical derived from the corresponding α-amino acid by eliminating the hydroxyl of the carboxy group and one hydrogen of the α-amino group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "halo" as used herein means a halogen radical selected from bromo, chloro, fluoro or iodo.

The term "$C_{1-6}$ alkyl" or "(lower)alkyl" as used herein, either alone or in combination with another radical, means straight chain or branched alkyl radicals containing up to six carbon atoms and includes, for example, methyl, ethyl, propyl, butyl, hexyl, 1-methylethyl, 1-methylpropyl, 2-methylpropyl, 1,1-dimethylethyl.

Likewise, the terms "$C_{1-3}$ alkyl" "$C_{1-4}$ alkyl" and "$C_{1-10}$ alkyl" are used to denote alkyl radials containing up to three, four and ten carbon atoms, respectively.

The term "$C_{3-7}$ cycloalkyl" as used herein, either alone or in combination with another radical, means a cycloalkyl radical containing from three to seven carbon atoms and includes cyclopropyl, cyclobutyl, cyclopentyl, cyclohexyl and cycloheptyl.

The term "$C_{4-10}$ (alkylcycloalkyl) as used herein means a cycloalkyl radical containing from three to seven carbon atoms linked to an alkyl radical, the linked radicals containing up to ten carbon atoms; for example, cyclopropylmethyl, cyclopentylethyl, cyclohexylmethyl, cyclohexylethyl or cycloheptylethyl.

The term "$C_{2-10}$ alkenyl" as used herein, either alone or in combination with another radical, means an alkyl radical as defined above containing from 2 to 10 carbon atoms, and further containing at least one double bond. For example alkenyl includes allyl.

The term "$C_{3-4}$ alkylene" as used herein means a divalent alkyl radical derived by the removal of two hydrogen atoms from a straight or branched chain aliphatic hydrocarbon containing from three to four carbon atoms and includes, for example, —CH$_2$CH$_2$CH$_2$—, CH(CH$_3$)CH$_2$CH$_2$—, —CH$_2$C(CH$_3$)$_2$— and —CH$_2$CH$_2$CH$_2$CH$_2$—.

The term "$C_{1-6}$ alkoxy" as used herein, either alone or in combination with another radical, means the radical —O—$C_{1-6}$ alkyl wherein alkyl is as defined above containing up to six carbon atoms. Alkoxy includes methoxy, ethoxy, propoxy, 1-methylethoxy, butoxy and 1,1-dimethylethoxy. The latter radical is known commonly as tert-butoxy.

The term "$C_6$ or $C_{10}$ aryl" as used herein, either alone or in combination with another radical, means either an aromatic monocyclic system containing 6 carbon atoms or an aromatic cyclic system containing 10 carbon atoms.

The term "$C_{7-16}$ aralkyl" as used herein, either alone or in combination with another radical, means an aryl as defined above linked through an alkyl group, wherein alkyl is as defined above containing from 1 to 6 carbon atoms. Aralkyl includes for example benzyl, and butylphenyl.

The term "carboxy(lower)alkyl" as used herein, either alone or in combination with another radical, means a carboxyl group (COOH) linked through a (lower)alkyl group as defined above and includes for example butyric acid or the groups:

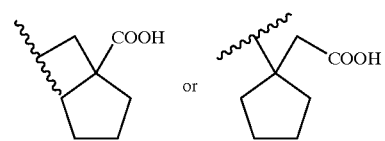

The term "cyclic" or "cyclic system" as used herein, either alone or in combination with another radical, means a monovalent radical derived by removal of a hydrogen from a saturated or unsaturated cyclic hydrocarbon, containing from three to seven carbon atoms, unless otherwise indicated and optioonally conctaing one or more heteroatom. The term cyclic or cyclic system includes, for example, cyclopropane, cyclopentane, cyclohexane, cyclohexene, decalin, tetralin, indene, and naphthalene.

The term "heterocycle" as used herein, either alone or in combination with another radical, means a monovalent radical derived by removal of a hydrogen from a five-, six-, or seven-membered saturated or unsaturated heterocycle containing from one to four heteroatoms selected from nitrogen, oxygen and sulfur. Examples of suitable heterocycles include: pyrrolidine, tetrahydrofuran, thiazolidine, pyrrole, thiophene, diazepine, 1H-imidazole, 1-methyl-1H-imidazole, isoxazole, thiazole, 2-methylthiazole, 2-aminothiazole, piperidine, 1,4-dioxane, 4-morpholine, pyridine, 2-methylpyridine, pyrimidine, 4-methylpyrimidine and 2,4-dimethylpyrimidine.

The term "heterocyclic system" as used herein, either alone or in combination with another radical, means a heterocycle as defined above fused to one or more other cycle be it a heterocycle or any other cycle.

Examples of suitable heterocyclic systems include: thiazolo[4,5-b]-pyridine, quinoline, or indole.

Preferred embodiments

A further preferred group of compounds are represented by formula I wherein B is preferably an acyl derivative of formula $R_{11}C(O)$— wherein $R_{11}$ is:

$C_{1-6}$ alkyl optionally substituted with carboxyl, $C_{1-6}$ alkanoyloxy or $C_{1-6}$ alkoxy;

$C_{3-7}$ cycloalkyl optionally substituted with carboxyl, MeOC(O), EtOC(O) or BnOC(O);

3-carboxypropionyl (DAD) or 4-carboxybutyryl (DAE); or

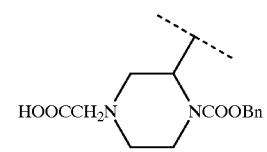

More preferably, B is acetyl, 3-carboxypropionyl, 4-carboxylbutyryl, AcOCH$_2$C(O), Me$_3$COC(O),

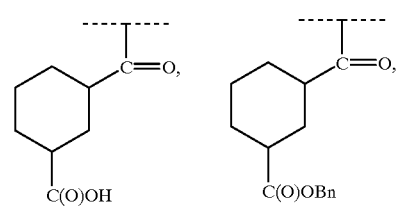

-continued

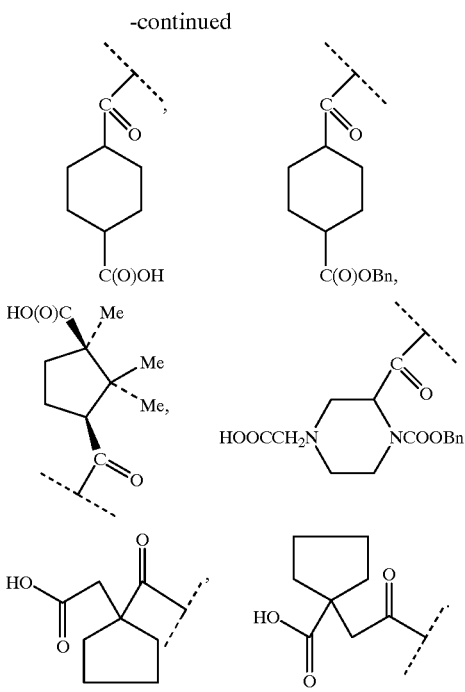

Still, more preferably, B is acetyl, 3-carboxypropionyl (DAD), 4—carboxybutyryl (DAE), AcOCH$_2$C(O),

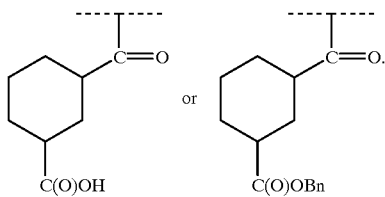

Most preferably, B is acetyl, or 4-carboxybutyryl (DAE). Preferably, B is acetyl.

Preferably, R$_6$, when present, is the side chain of Asp or Glu.

Most preferably, R$_6$, when present, is the side chain of Asp.

Alternatively, preferably, a is 0 and then R$_6$ is absent.

Preferably, R$_5$, when present, is the side chain of an amino acid selected from the group consisting of: D-Asp, L-Asp, D-Glu, L-Glu, D-Val, L-Val, D-tert-butylglycine (Tbg), and L-Tbg.

More preferably, R$_5$, when present, is the side chain of D-Asp, D-Val, or D-Glu.

Most preferably, R$_5$, when present, is the side chain of D-Glu.

Alternatively, preferably a is 0 and b is 0, and then both R$_6$ and R$_5$ are absent.

Preferably, Y is H or C$_{13}$ alkyl.
More preferably, Y is Me.
Alternatively, more preferably Y is H.
Preferably, R$_4$ is the side chain of an amino acid selected from the group consisting of: Val, cyclohexylglycine (Chg), Tbg, Ile, or Leu.

More preferably, R$_4$ is the side chain of Chg or Ile.
Most preferably, R$_4$ is the side chain of Chg.
Preferably, R$_3$ is the side chain of an amino acid selected from the group consisting of: Ile, Chg, Cha, Val or Glu.
More preferably, R$_3$ is the side chain of Val or Chg.

Most preferably, R$_3$ is the side chain of Val.
Preferably, W is a group of formula II:

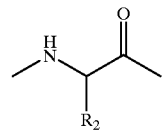

wherein R$_2$ is C$_{1-8}$ alkyl and C$_{3-6}$ cycloalkyl optionally substituted with carboxyl; or benzyl. More preferably, R$_2$ is the side chain of Asp, aminobutyric acid (Abu) or Val.

Still, more preferably, W is a group of formula II':

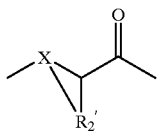

wherein preferably, X is CH or N.
More preferably R$_2$' is a C$_3$ or C$_4$ alkylene (shown in black) that joins X to form a 5- or 6-membered ring of formula III:

Formula III

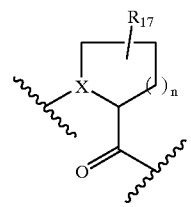

R$_2$' being optionally substituted at any position with R$_{17}$, wherein X is CH or N; n is 1 or 2, and R$_{17}$ is as defined below.

Most preferably, X is N. For example, preferably R$_2$' is propylene joined to X wherein X is nitrogen to form a proline substituted with R$_{17}$ at P2.

Most preferably R$_2$' is the side chain of proline substituted at the 3-, 4-, or 5-position with R$_{17}$, wherein R$_{17}$ is as defined below.

Still, most preferably R$_2$' is the side chain of proline (as shown in black) substituted with R$_{17}$ at the 4-position with the stereochemistry shown in formula III':

Formula III'

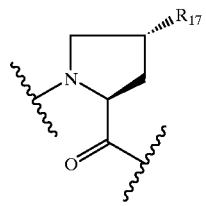

wherein R$_{17}$ is preferably OH; SH; NH$_2$; carboxyl; R$_{12}$; OR$_{12}$, SR$_{12}$, NHR$_{12}$ or NR$_{12}$R$_{12}$' wherein R$_{12}$ and R$_{12}$' are independently:

cyclic C$_{3-16}$ alkyl or acyclic C$_{1-16}$ alkyl or cyclic C$_{3-16}$ alkenyl or acyclic C$_{2-16}$ alkenyl, said alkyl or alkenyl optionally substituted with NH$_2$, OH, SH, halo, or carboxyl; said alkyl or alkenyl optionally containing at least one heteroatom independently selected from the group consisting of: O, S, and N; or $R_{12}$ and $R_{12}'$ are independently $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl; said aryl or aralkyl optionally containing at least one heteroatom independently selected from the group consisting of: O, S, and N;

said cyclic alkyl, cyclic alkenyl, aryl or aralkyl being optionally fused with a second 5-, 6- or 7-membered ring to form a cyclic system or heterocycle, said second ring being optionally substituted with $NH_2$, OH, SH, halo, carboxyl or carboxy(:lower)alkyl; said second ring optionally containing at least one heteroatom independently selected from the group consisting of: O, S, and N.

More preferably, $R_{17}$ is $OR_{12}$ wherein $R_{12}$ is a $C_6$ or $C_{10}$ aryl or $C_{7-16}$ aralkyl, said first aryl or aralkyl optionally substituted with $C_{1-6}$ alkyl, $C_{3-7}$ cycloalkyl, $NH_2$, OH, SH, halo, $C_{1-6}$ alkoxy, carboxyl, carboxy(lower)alkyl, or a second aryl or aralkyl; said first and second aryl or aralkyl optionally containing at least one heteroatom selected independently from the group consisting of: O, S, and N.

Most preferably, $R_{17}$ is Bn; $PhCH_2CH_2$; $PhCH_2CH_2CH_2$; O—Bn; o-tolylmethoxy; m-tolylmethoxy; p-tolylmethoxy; 1-naphtyloxy; 2-naphtyloxy; 1-naphthalenylmethoxy; 2-naphthalenylmethoxy; (4-tert-butyl)methoxy; (3I—Ph)CH$_2$O; (4Br—Ph)O; (2Br—Ph)O; (3Br—Ph)O; (4I—Ph)O; (3Br—Ph)CH$_2$O; (3,5—Br$_2$—Ph)CH$_2$O;

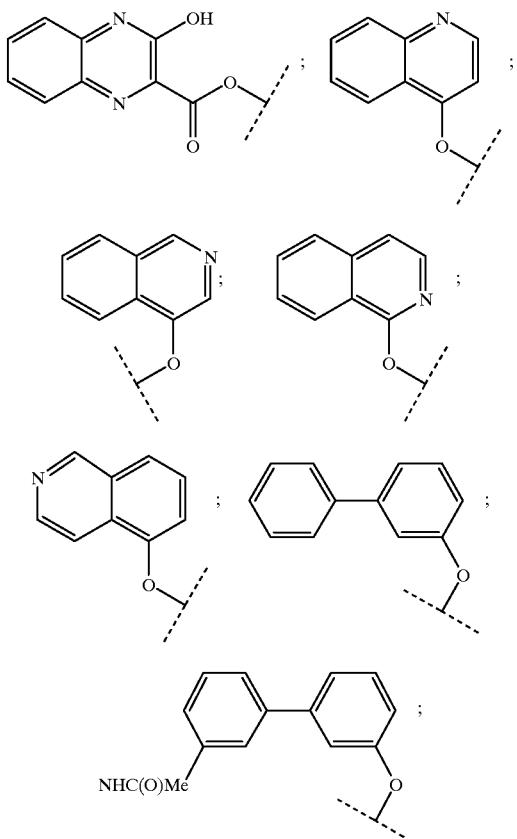

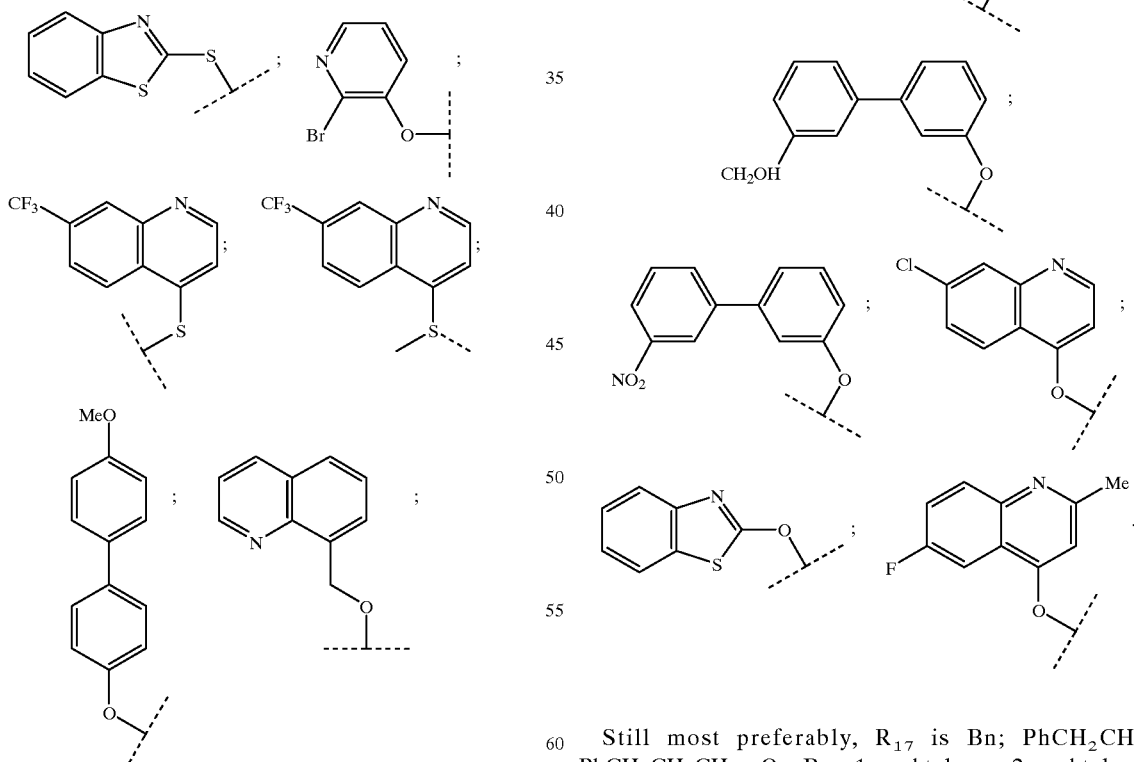

Still most preferably, $R_{17}$ is Bn; $PhCH_2CH_2$; $PhCH_2CH_2CH_2$; O—Bn; 1-naphtyloxy; 2-naphtyloxy; 1-naphthalenylmethoxy; 2-naphthalenylmethoxy;

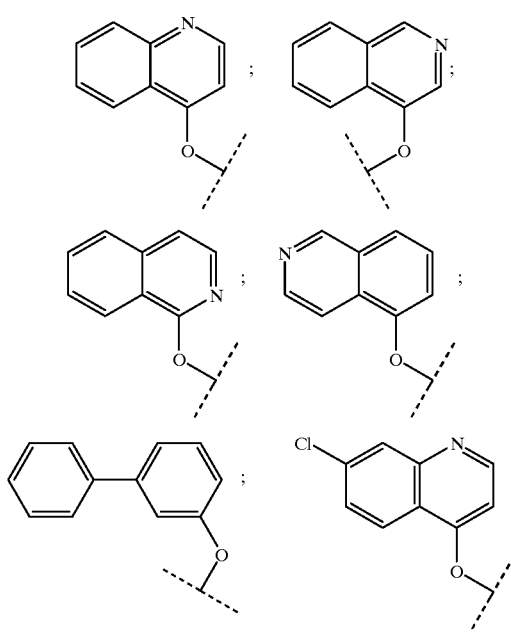

Even most preferably, $R_{17}$ is O—Bn, 1-naphthalenylmethoxy, or 2-naphthalenylmethoxy.

Preferably Q is:

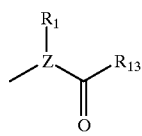

wherein Z is preferably CH or N.

Preferably, when Z is CH:

$R_{13}$ is H; $CF_3$; $CF_2CF_3$; $CH_2$—$R_{14}$; C(O)NH—$R_{14}$; $NR_{14}R_{14}$, wherein $R_{14}$ and $R_{14}$, are as defined above with the proviso that $R_{13}$ is not an α-amino acid or an ester thereof. More preferably $R_{13}$ is H; NH—$R_{14}$ or C(O)NH—$R_{14}$. Most preferably, $R_{13}$ is H; or C(O)NH—$R_{14}$. Preferably $R_{14}$ is phenyl or $C_{7-16}$ aralkyl. More preferably, $R_{14}$ is benzyl or CH(Me)Ph.

Alternatively, when Z is N:

$R_{13}$ is preferably phenyl, or $C_{7-16}$ aralkyl,

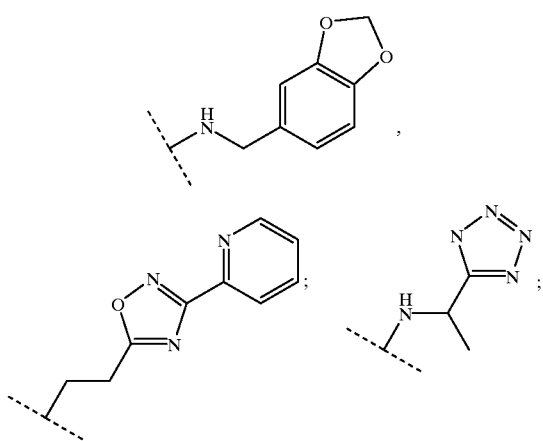

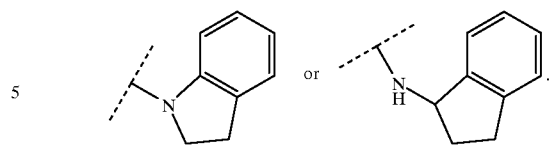

More preferably, $R_{13}$ is naphthyl, NH—CH(Me)Ph, NH—CH(Et)Ph,

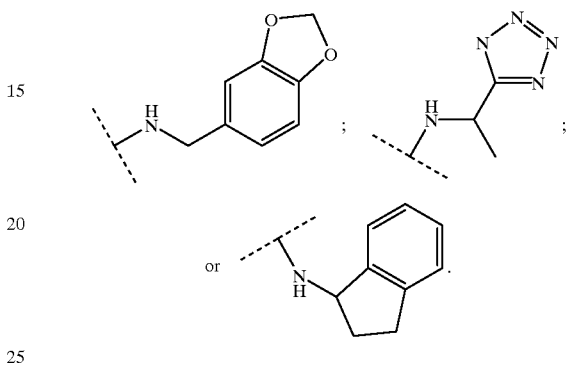

Most preferably, $R_{13}$ is, N:H—CH(Me)Ph, or

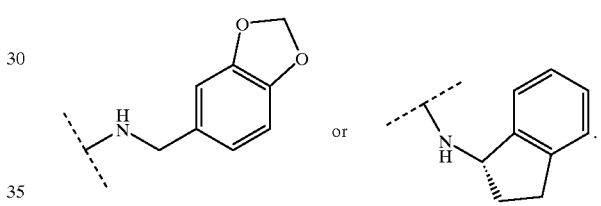

Alternatively, Q is preferably a phosphonate group of the formula:

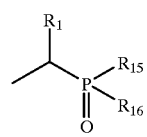

wherein $R_{15}$ and $R_{16}$ are independently preferably $C_{6-12}$ aryloxy. More preferably, $R_{15}$ and $R_{16}$ are each phenoxy.

In all of the above cases, $R_1$ is preferably $C_{1-6}$ alkyl or $C_{1-6}$ alkenyl optionally substituted with halo.

More preferably, $R_1$ is $C_{1-5}$ alkyl or $C_{1-4}$ alkenyl optionally substituted with fluoro. Most preferably, $R_1$ is ethyl, propyl, isopentyl, or allyl.

According to an alternate embodiment, the pharmaceutical compositions of this invention may additionally comprise an antiviral agent. Examples of antiviral agents include, ribavirin and amantadine.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, such as helicase, polymerase, or metalloprotease.

The pharmaceutical compositions of this invention may be administered orally, parenterally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example. Tween 80) and suspending agents.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, $19^{th}$ Ed. Mack Publishing Company, Easton, Pa., (1995).

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS3 protease; inhibitors of other targets in the HCV life cycle such as helicase, polymerase, metalloprotease, or internal ribosome entry; or combinations thereof. The additional agents may be combined with the compounds of this invention to create a single dosage form. Alternatively these additional agents may be separately administered to a mammal as part of a multiple dosage form.

Accordingly, another embodiment of this invention provides methods of inhibiting HVC NS3 protease activity in mammals by administering a compound of the formula I, wherein the substituents are as defined above.

In a preferred embodiment, these methods are useful in decreasing HCV NS3 protease activity in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metallo protease. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing HCV disease. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the composition according to this invention.

The compounds set forth herein may also be used as laboratory reagents. The compounds of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Process

Synthesis of P6-P2 fragments

The P2-P6 fragments of the compounds of the present invention were synthesized according to the process as illustrated in scheme I (wherein PG1 is a carboxyl protecting group and PG2 is an amino protecting group):

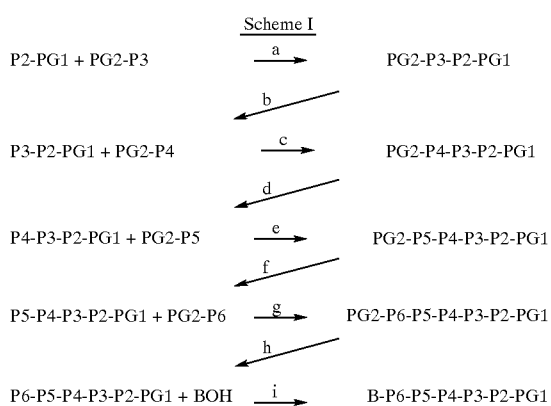

Briefly, the P2, P3, P4, and optionally P5 and P6 can be linked by well known peptide coupling techniques. The P2, P3, P4, and P5 and P6 moieties may be linked together in any order as long as the final compound corresponds to peptides of formula I. For example, P6 can be linked to P5 to give P5-P6 that is linked to P4-P3-P2; or P6 linked to P5-P4-P3 then linked to an appropriately C-terminal protected P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I, or by condensation of fragments (two or several amino acids), or combination of both processes, or by solid phase peptide synthesis according to the method originally described in Merrifield, J. Am. Chem. Soc., (1963), 85, 2149–2154, the disclosure of which is hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

More explicitly, the coupling step involves the dehydrative coupling of a free carboxyl of one reactant with the free amino group of the other reactant in the presence of a coupling agent to form a linking amide bond. Description of such coupling agents are found in general textbooks on peptide chemistry, for example, M. Bodanszky, "Peptide Chemistry", 2nd rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A very practical and useful coupling agent is the commercially available (benzotriazol-1-yloxy)tris-(dimethylamino)phosphonium hexafluorophosphate, either by itself or in the presence of 1-hydroxybenzotriazole. Another very practical and useful coupling agent is commercially available 2-(1H-benzotriazol-1-yl)-N,N,N',N'-tetramethyluronium tetrafluoroborate. Still another very practical and useful coupling agent is commercially available O—(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated. In addition to the foregoing, other methods of peptide synthesis are described in Stewart and Young, "Solid Phase Peptide Synthesis", $2^{nd}$ ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980–1987); Bodansky et al., "The Practice of Peptide Synthesis" Springer-Verlag, New-York (1984), the disclosures of which are hereby incorporated by reference.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-carboxyl group of the C-terminal residue is usually protected as an ester (PG1) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The α-amino group of each amino acid to be coupled to the growing peptide chain must be protected (PG2). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (RT).

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, p-toluenesulfonyl (tosyl) is suitable to protect the amino side chain of amino acids such as Lys and Arg; acetamidomethyl, benzyl (Bn), or t-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

When a solid phase synthesis is used, the peptide is cleaved from the resin simultaneously with the removal of the protecting groups. When the Boc protection method is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection method is used the N-terminal Fmoc group is cleaved with reagents described earlier. The other protecting groups and the peptide are cleaved from the resin using solution of trifluoroacetic acid and various additives such as anisole, etc.

Synthesis of capping group B and P6, P5, P4, and P3 moieties

Different capping groups B are introduced to protected P6, P5, P4, the whole peptide or to any peptide segment with an appropriate acyl chloride that is either available commercially or for which the synthesis is well known in the art. Different P6 to P3 moieties are available commercially or the synthesis is well known in the art.

Synthesis of P2 moieties

1. Synthesis of precursors:

A) Synthesis of haloarylmethane derivatives.

The preparation of halomethyl-8-quinoline IId was done according to the procedure of K. N. Campbell et al., J. Amer. Chem. Soc., (1946), 68, 1844.

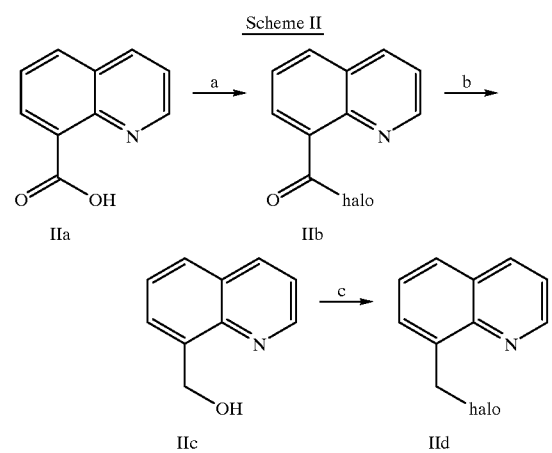

Scheme II

Briefly, 8-quinoline carboxylic acid IIa was converted to the corresponding alcohol IIc by reduction of the corresponding acyl halide IIb with a reducing agent such as lithium aluminium hydride. Treatment of alcohol IIb with the appropriate hydrohaloacid gives the desired halo derivative IId. A specific embodiment of this process is presented in Example 1.

2. Synthesis of P2:

A) The synthesis of 4-substituted proline (wherein $R_{17}$ is attached to the ring via a carbon atom) (with the stereochemistry as shown):

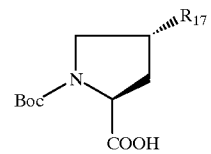

is done as shown in Scheme III according to the procedures described by J. Ezquerra et al. (Tetrahedron, (199,), 38, 8665–8678) and C.

Pedregal et al. (Tetrahedron Lett., (1994), 35, 2053–2056).

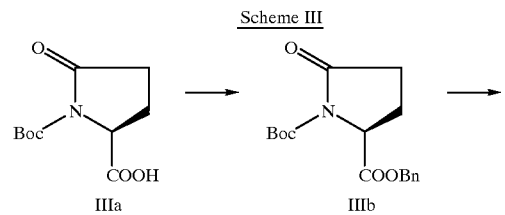

Scheme III

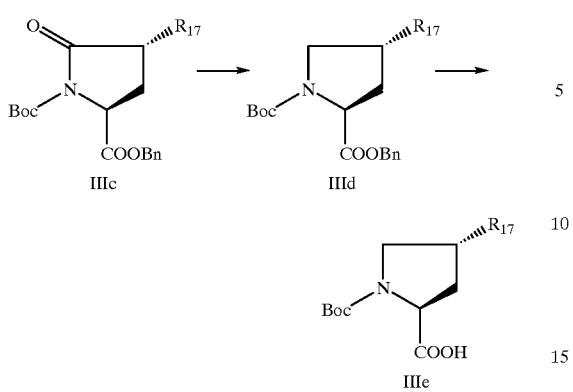

Briefly, Boc-pyroglutamic acid is protected as a benzyl ester. Treatment with a strong base such as lithium diisopropylamide followed by addition of an alkylating agent (Br—$R_{17}$ or I—$R_{17}$) gives the desired compounds IIIe after reduction of the amide and deprotection of the ester. A specific embodiment of this process is presented in Example 2.

B) The synthesis of O-alkylated 4-(R)-hydroxyproline:

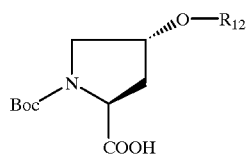

may be carried out using the different processes described below.

B.1) When $R_{12}$ is aralkyl, the process can be carried out according to the procedure described by E. M. Smith et al. (J. Med. Chem. (1988), 31, 875–885). Briefly, commercially available Boc- 4(R)-hydroxyproline is treated with a base such as sodium hydride and the resulting alkoxide reacted with an alkrylating agent (Br—$R_{12}$ or I—$R_{12}$) to give the desired compounds. Specific embodiments of this process are presented in Examples 3 and 4.

B.2) When $R_{12}$ is aryl, the compounds can be prepared via a Mitsunobu reaction (Mitsunobu (1981), Synthesis, January, 1–28; Rano et al., (1995), Tet. Lett. 36(22), 3779–3792; Krchnak et al., (1995), Tet. Lett. 36(5), 62193–6196; Richter et al., (1994), Tet. Lett. 35(27), 4705–4706). Briefly, commercially available Boc-4(S)-hydroxyproline methyl ester is treated with the appropriate aryl alcohol or thiol in the presence of triphenylphosphine and diethylazodicarboxylate (DEAD) and the resulting ester is hydrolysed to the acid. Specific embodiment of this process are presented in Example 5.

Scheme IV

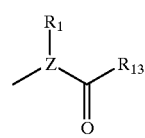

Alternatively, the Mitsunobu reaction can be performed on solid phase (as shown in Scheme IV). The 96-well block of the Model 396 synthesizer (advanced ChemTech) is provided with aliquots of resin-bound compound (IVa) and a variety of aryl alcohols or thiols and appropriate reagents are added. After incubation, each resin-bound product (IVb) is washed, dried, and cleaved from the resin.

B.2.a) A Suzuki reaction (Miyaura et al., (1981), Synth. Comm. 11, 513; Sato et al., (1989), Chem. Lett., 1405; Watanabe et al., (1992), Synlett., 207; Takayuki et al., (1993), J. Org. Chem. 58, 2201; Frenette et al., (1994), Tet. Lett. 35(49), 9177–9180; Guiles et al., (1996), J. Org. Chem. 61, 5169–5171) can also be used to further functionalize the aryl substituent.

C) Synthesis of compounds; of formula I wherein Q is:

wherein Z is CH; $R_1$ is as defined above and $R_{13}$ is $CF_3$, $CF_2CF_3$ or $C(O)NH$—$R_{14}$; was done as described in Scheme VIII.

The synthesis of the required P1 moieties was done as follows:

i) For the synthesis of trifluoromethyl alcohols of formula Vd the procedure described by J. W. Skiles et al. (J. Med. Chem. (1992), 35, 641–662) was used as illustrated:

Scheme V

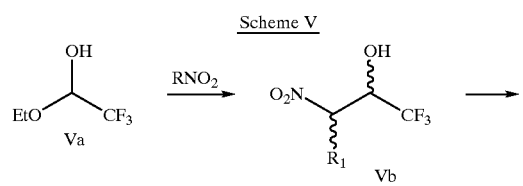

-continued

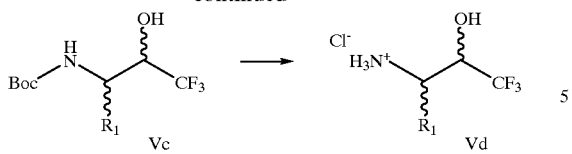

wherein $R_1$ is as defined above.

Briefly, a condensation between commercially available trifluoroacetaldehyde ethyl hemiacetal Va and the appropriate nitroalkane affords the corresponding nitroalcohol Vb. The nitro group was reduced (preferably with Ra—Ni) and protected as the Boc-derivative Vc to allow easier purification of the fragment. Treatment of the Boc-amine with anhydrous HCl affords the hydrochloride salt Vd.

ii) For the synthesis of pentafluoroethyl alcohols of formula VId, the procedure described by M. R. Angelastro et al. (J. Med. Chem., (1994), 37, 4538–4554) was used as illustrated in scheme VI:

Scheme VI

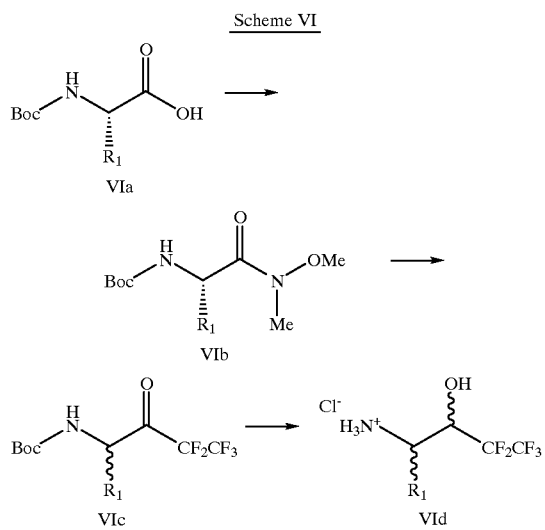

wherein $R_1$ is as defined above.

Briefly, the Boc-amino acid VIa was converted to the Weinreb amide VIb according to the procedure described by Castro, B. et al. (Synthesis, (1983), 676–678) and treated with lithium pentafluoroethane. The resulting pentafluoroethyl ketone VIc was reduced and the Boc protecting group removed with anhydrous HCl to give the hydrochloride salt of the desired amino alcohol VId.

iii) For the synthesis of hydroxy amides of formula VIIf the procedure described by Peet et al. (Tet. Lett. (1988), 3433) was used as illustrated in scheme VII:

Scheme VII

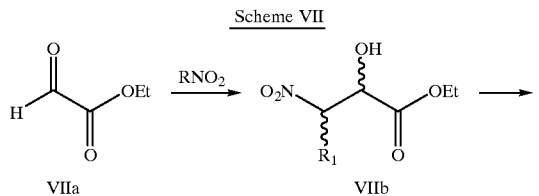

-continued

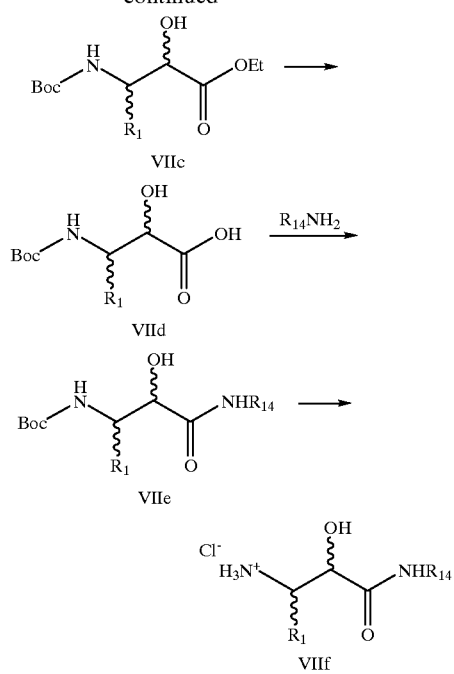

wherein $R_1$ is as defined above.

Briefly, condensation between ethyl glyoxylate VIIa and a nitroalkane under basic conditions afforded the corresponding nitroalcohol VIIb. The nitro group was reduced (preferably with Ra—Ni) and protected as the Boc-derivative VIIc. Saponification of the ester group followed by standard coupling with an amine gave the hydroxy amide VIIe. Removal of the Boc protecting group with anhydrous HCl afforded the hydrochloride salt of the desired amino hydroxyamide VIIf.

iv) The coupling to P2-P6 was carried out as illustrated in scheme VIII:

Scheme VIII

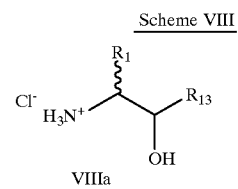

COUPLING OF
a | P2-P3-P4-[P5]-[P6]-B FRAGMENT a) The P6 to P2 fragment can be linked to the free amino group of the amino alcohol derivative VIIIa as described previously in Scheme I to give the peptido alcohol VIIIb.
b) The alcohol functionality of the peptido alcohol VIIb is then oxidized by techniques and procedures well known and appreciated by one of ordinary skill in the art, such as the Swern Oxidation (Tidwell, T. T., Synthesis, (1990), 857–870), or more specifically the Pfitzner-Moffatt oxidation (K. E. Pfitzner, and J. G. Moffatt, J. Am. Chem. Soc., (1965), 5670–5678) and the Dess-Martin periodinane method (D. B. Dess or J. C. Martin, (J. Org. Chem., (1983), 48, 4155–4156) to give the compounds of formula I wherein Q contains an activated carbonyl.

D) Synthesis of compounds of formula I wherein Q is:

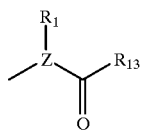

wherein Z is N; and $R_{13}$ is $NHR_{14}$, $NR_{14}R_{14}'$, $CH_2$—$R_{14}$, $CHR_{14}R_{14}'$ or $O$—$R_{14}$; wherein $R_{14}$ and $R_1$ are as defined above, was done as described in scheme X.

i) For the synthesis of the aza-containing P1 fragments, the procedure described by A. S. Dutta et al. (J. Chem. Soc. Perkin I, (1975), 1712) was followed as illustrated:

Scheme IX

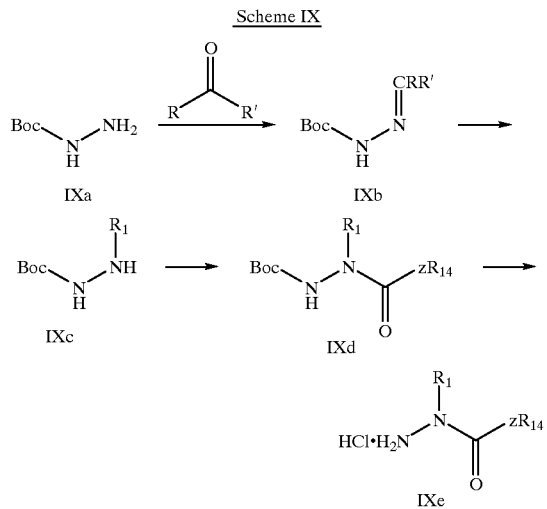

z = O, NH, CH2 wherein $R_1$ and $R_{14}$ are as defined hereinabove.

Briefly, commercially available Boc hydrazine IXa was treated with an appropriate aldehyde or ketone to afford the corresponding hydrazone IXb. The hydrazone was reduced (preferentially with DIBAL) to give the alkyl carbazate IXc. Treatment of the alkyl carbazate with isocyanates affords the corresponding aza peptide fragment (IXd, wherein z=NH). Treatment of the alkyl carboxate with carbamoyl chlorides afford the corresponding aza peptide fragment (XXd, wherein z=$NR_{14}R_{14'}$). Treatment of the alkyl carbazate with chloroformates afford the aza-carbamate (IXd, wherein z=O) while treatment with acid chlorides affords the carbon analogues (IXd, wherein z=$CH_2$). Alternatively, treatment of the alkyl carbazate with carboxylic acids using standard coupling conditions affords the corresponding aza peptide fragment (IXd, wherein Z=$CHR_{14'}$, or $CH_2$) Finally the Boc-protecting group was removed with anhydrous HCl to give the desired aza-derivatives IXe.

ii) Coupling of P2-P6 was carried out according to scheme X:

Scheme X

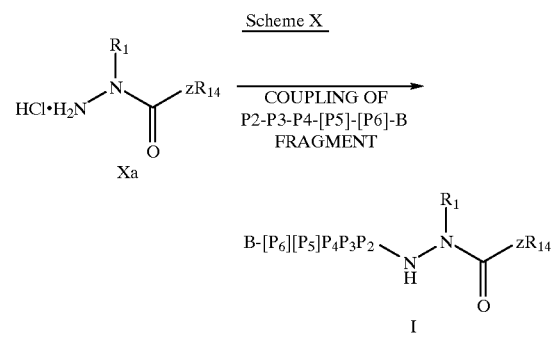

wherein z is O, NH, $CH_2$, $CHR_{14'}$, or $NR_{14''}$.

The P6 to P2 fragment can be linked to the free amino group of derivative Xa as described previously in Scheme I to give the aza-derivatives of formula I wherein Z is N.

E) Synthesis of compounds of formula I wherein Q is:

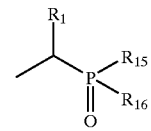

wherein $R_{15}$ and $R_{16}$ are as defined above, the procedure described by J. Oleksyszyn et al. (Synthesis, (1979), 985–1386) was used as illustrated in scheme XI:

Scheme XI

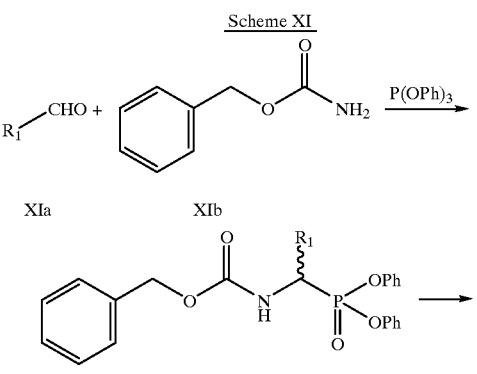

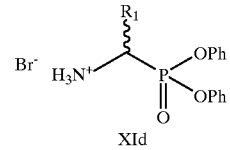

wherein $R_1$ is as defined hereinabove.

Briefly, a two step synthesis of the diphenyl ester was accomplished by condensation of a suitable aldehyde XIa, benzyl carbamate XIb, and triphenyl phosphite in the presence of acetic acid. Removal of the benzyloxycarbonyl protecting group of XIc using HBr/AcOH afforded the desired hydrobromide salt XId.

The P6 to P2 fragment can be linked to the free amino group of phosphonate derivative of formula XId as described previously in Scheme I to give the phophonopeptide of formula I wherein Q is a phosphonate moiety.

The following examples are provided to describe the invention in further detail. These examples, which set forth the best mode presently contemplated for carrying out the invention, are intended to illustrate and not to limit the invention.

EXAMPLES

The present invention is illustrated in further detail by the following non-limiting examples.

Temperatures are given in degrees Celsius (° C). Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

Abbreviations used in the examples include Bn: benzyl; Boc: tert-butyloxycarbonyl {$Me_3COC(O)$}; BSA: bovine serum albumin; CHAPS: 3-[(3-cholamidopropyl)-dimethylammonio]-1-propanesulfonate; DBU: 1,8-diazabicyclo[5.4.0]undec-7-ene; $CH_2Cl_2$=DCM: methylene chloride; DIAD: Diisopropyl azodicarboxylate; DIPEA: diisopropylethylamine; DMAP: dimethylaminopyridine; DCC: 1,3-dicyclohexyl-carbodiimide; DME: 1,2-dimethyoxyethane; DMF: dimethylformamide; DMSO: dimethylsulfoxide; DTT: dithiothreitol or threo-1,4-dimercapto-2,3-butanediol; EDTA: ethylenediaminetetraacetic acid; Et: ethyl; EtOH: ethanol; EtOAc: ethyl acetate; $Et_2O$: diethyl ether; HPLC: high performance liquid chromatography; MS: mass spectrometry (MALDI-TOF: Matrix Assisted Laser Disorption Ionisation-Time of Flight, FAB: Fast Atom Bombardment);LAH: lithium aluminum hydride; Me: methyl; MeOH: methanol; MES: (2-{N-morpholino}ethane-sulfonic acid); NaHMDS: sodium bis(trimethylsilyl)amide; NMM: N-methylmorpholine; NMP: N-methylpyrrolidine; Pr: propyl; Succ: 4-hydroxy-1,4-dioxobutyl; PNA: 4-nitrophenylamino or p-nitroanalide; TBAF: tetra-n-butylammonium fluoride; TCEP: tris(2-carboxyethyl) phosphine hydrochloride; TFA: trifluoroacetic acid; THF: tetrahydrofuran; TIS: triisopropylsilane; TLC: thin layer chromatography; TMSE: trimethylsilylethyl; Tris/HCl: tris(hydroxymethyl)aminomethane hydrochloride.

Example 1
Synthesis of bromomethyl-8-quinoline (1):

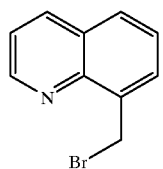

(1)

To commercially available 8-quinoline carboxylic acid (2.5 g, 14.4 mmol) was added neat thionyl chloride (10 ml, 144 mmol). This mixture was heated at 80° C. for 1 h before the excess thionyl chloride was distilled off under reduced pressure. To the resulting brownish solid was added absolute EtOH (15 mL) which was heated at 80° C. for 1 h before being concentrated in vacuo. The residue was partitioned between EtOAc and saturated aqueous $NaHCO_3$, and the organic phase dried ($MgSO_4$), filtered and concentrated to give a brownish oil (2.8 g). This material (ca. 14.4 mmol) was added dropwise over 35 min to a LAH (0.76 g, 20.2 mmol)/$Et_2O$ suspension which was cooled to −60° C. The reaction mixture was slowly warmed to −35° C. over 1.5 h before the reaction was complete. The reaction was quenched with $MgSO_4.10H_2O$ slowly over 30 min and then wet THF. The mixture was partitioned between $Et_2O$ and 10% aqueous $NaHCO_3$. The organic phase was dried ($MgSO_4$), filtered and concentrated to give a yellowish solid (2.31 g, 80% over 2 steps) corresponding to the alcohol. The alcohol (2.3 g, 11.44 mmol) was dissolved in AcOH/HBr (20 mL, 30% solution from Aldrich) and heated at 70° C. for 2.5 h. The mixture was concentrated in vacuo to dryness, partitioned between EtOAc (100 mL) and saturated aqueous $NaHCO_3$ before being dried ($MgSO_4$), filtered and concentrated to give the desired compound (1) as a brownish solid (2.54 g, 100%).

Example 2
Synthesis of Boc-4(R)-(3-phenylpropyl)proline (2d).

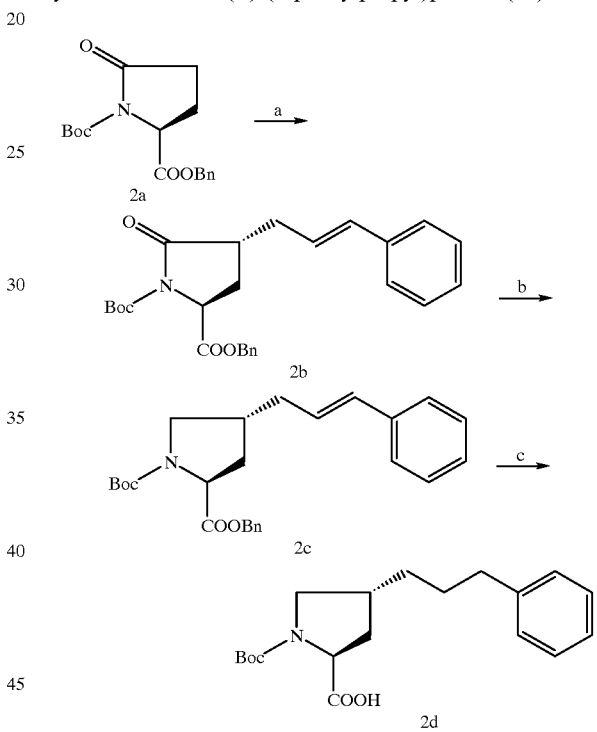

a) Synthesis of compound 2b:
To a solution of Boc-pyroglutamic acid benzyl ester (2a) (prepared as described by A. L Johnson et al., J. Med. Chem. (1985), 28, 1596–1602) (500 mg, 1.57 mmol) in THF (10 mL) at −78° C., was slowly added lithium hexamethydisilylazide (1.72 mL, 1M solution in THF). After stirring for 1 h at −78° C., cinnamyl bromide (278 μL, 1.88 mmol) was added and the stirring continued for an additional 2 h. The reaction mixture was quenched with saturated ammonium chloride solution and extracted with ethyl ether (3×20 mL). The combined organic extracts were dried ($MgSO_4$), filtered and concentrated. The residue was purified by flash column chromatography (8:2 hexane:ethyl acetate) to give compound 2b as an off-white solid (367 mg, 54% yield). $^1$H NMR ($CDCl_3$): δ 7.35–7.19 (m, 10H), 6.43 (d, J=15 Hz, 1H), 6.11 (ddd, J=15, J'=J"=8 Hz, 1H), 5.26 (d, J=16 Hz, 1H), 5.17 (d, J=16 Hz, 1H), 4.59 (dd, J=9.5, J'=2 Hz, 1H), 2.83–2.70 (m, 2H), 2.41–2.34 (m, 1H), 2.22–2.16 (m, 1H), 2.10–2.02 (m, 1H) 1.42 (s, 9H).

b) Synthesis of compound 2c:

At −78° C., lithium triethylborohydride (1M solution in THF, 1.01 mL, 1.01 mmol) was added to a solution of compound 2b (367 mg, 0.843 mmol) in THF (5 mL), under a nitrogen atmosphere. After 30 min, the reaction mixture was quenched with saturated aqueous $NaHCO_3$ (2 mL) and warmed to 0° C. 30% $H_2O_2$ (5 drops) was added and the mixture was stirred at 0° C. for 20 min. The organic volatiles were removed in vacuo, and the aqueous layer was extracted with $CH_2Cl_2$ (3×10 mL). The combined organic extracts were dried ($MgSO_4$), filtered and concentrated. To a cold (−78° C.) solution of the residue and triethylsilane (134 μL, 0.843 mmol) in $CH_2Cl_2$ (3 mL) boron trifluoride etherate (118 μL, 0.927 mmol) was added dropwise under an atmosphere of nitrogen. After 30 min, additional triethylsilane (134 μL) and boron trifluoride etherate (118 μL) were added. After stirring for 2 h at −78° C., the reaction mixture was quenched with saturated aqueous $NaHCO_3$ (2 mL) and extracted with DCM (3×10 mL). The combined organic extracts were dried ($MgSO_4$), filtered and concentrated. The crude product was purified by flash column chromatography (8:2 hexane:ethyl acetate) to give compound 2c as a colorless oil (140 mg, 40% yield). $^1$H NMR ($CDCl_3$) indicated the presence of two rotamers: δ 7.34–7.22 (m, 10H), 6.38 (d, J=15.5 Hz, 1H), 6.15–6.08 (m, 1H), 5.29–5.07 (m, 2H), 4.44 (d, J=7 Hz, 1/3H), 4.33 (d, J=7 Hz, 2/3H), 3.76 (dd, J=10.5, J'=8.5 Hz, 2/3H), 3.69 (dd, J=10.5, J'=8.5 Hz, 1/3H), 3.13 (dd, J=9, J'=8.5 Hz, 2/3H) 3.05 (dd, J=9, J=8.5 Hz, 1/3H), 2.47–2.40 (m, 1H), 2.35–2.22 (m, 2H) 2.15–1.85 (m, 2H), 1.45 (s, (3/9) 9H), 1.33 (s, (6/9) 9H).

c) Synthesis of compound 2d:

To a solution of compound 2c (140 mg, 0.332 mmol) in ethanol (4 mL) was added 10% palladium on charcoal (30 mg). The mixture was stirred under an atmosphere of hydrogen for 2 h. The catalyst was removed by passing the mixture through a Millipore: Millex—HV 0.45 μm filter. The clear solution was concentrated to give the desired compound 2d as a colorless oil (115 mg, quant. yield). $^1$H NMR (DMSO-$d_6$) indicated the presence of two rotamers: δ 7.28–7.14 (m, 5H), 4.33 (br.s, 1H), 4.06–4.10, (m, 1H), 3.56–3.42 (m, 3H), 2.89–2.79 (m, 1H), ), 2.53–2.49 (m, 1H, under DMSO-$d_6$), 2.24–2.10 (m, 1H), 2.03–1.93 (m, 1H), 1.87–1.75 (m, 1H), 1.62–1.45 (m, 2H), 1.38 (s, (3/9) 9H), 1.33 (s, (6/9) 9H).

Example 3
Synthesis of Boc-4(R)-(naphthalen-1-ylmethoxy) proline (3):

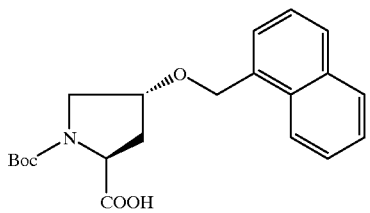

(3)

Commercially available Boc-4(R)-hydroxyproline (5.00 g, 21.6 mmol) was dissolved in THF (100 mL) and cooled to 0° C. Sodium hydride (60% dispersion in oil, 1.85 g, 45.4 mmol) was added portionwise over 10 minutes and the suspension was stirred at RT for 1 h. Then, 1-(bromomethyl) naphthalene (8.00 g, 36.2 mmol) (prepared as described in E. A. Dixon et al. Can. J. Chem., (1981), 59, 2629–2641) was added and the mixture was heated at reflux for 18 h. The mixture was poured into water (300 mL) and washed with hexane. The aqueous layer was acidified with 10% aqueous HCl and extracted twice with ethyl acetate. The organic layers were combined and washed with brine, dried ($MgSO_4$), filtered and concentrated. The residue was purified by flash chromatography (49:49:2 hexane: ethyl acetate: acetic acid) to give the title compound as a colorless oil (4.51 g, 56% yield). $^1$H NMR (DMSO-$d_6$) indicated the presence of two rotamers: δ 8.05 (m, 1H), 7.94 (m, 1H), 7.29 (d, J=14 Hz, 1H), 7.55–7.45 (m, 4H), 4.96 (m, 2H), 4.26 (br. s, 1H), 4.12 (dd, J=J=8 Hz, 1H), 3.54–3.42 (m, 2H), 2.45–2.34 (m, 1H), 2.07–1.98 (m, 1H:) 1.36 (S, (3/9) 9H), 1.34 (s, (6/9) 9H).

Example 4

Synthesis of Boc-4(R)-(8-quinoline-methyloxy) proline (4):

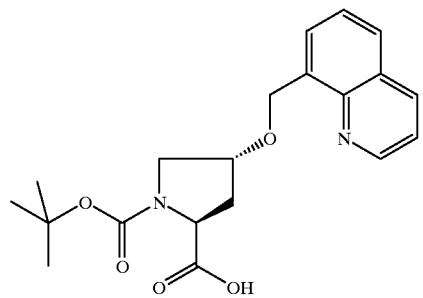

(4)

Boc-4(R)-hydroxyproline (1.96 g, 8.5 mmol) in anhydrous THF (20 mL) was added to a suspension of NaH (1.4 g, 60% in oil, :34 mmol) in THF (100 mL). This mixture was stirred 30 min before bromomethyl-8-quinoline from Example 1 (2.54 g, 11.44 mmol) was added in THF (30 mL). The reaction mixture was heated at 70° C. (5 h) before the excess NaH was destroyed carefully with wet THF. The reaction was concentrated in vacuo and the resulting material was dissolved in EtOAc and $H_2O$. The basic aqueous phase was separated and acidified with 10% aqueous HCl to pH ~5 before being extracted with EtOAc (150 mL). The organic phase was dried ($MgSO_4$), filtered and concentrated to give a brown oil. Purification by flash chromatography (eluent: 10% MeOH/$CHCl_3$) gave the desired compound as a pale yellow solid (2.73 g, 86%). HPLC (97.5%); $^1$H-NMR (DMSO-$d_6$) shows rotamer populations in a 6:4 ratio, δ 12–11.4 (bs, 1H), 8.92 (2×d, J=4.14 and 4.14 Hz, 1H), 8.38 (2×d, J=8.27 and 8.27 Hz, 1H), 7.91 (d, J=7.94 Hz, 1H), 7.77 (d, J=7.0 Hz, 1H), 7.63–7.54 (m, 2H), 5.14 (2×s, 2H), 4.32–4.29 (m, 1H), 4.14–4.07 (m, 1H), 3.52–3.44 (m, 2H), 2.43–2.27 (m, 1H), 2.13–2.04 (m, 1H), 1.36 and 1.34 (2×s, 9H).

Example 5
Preparation of Boc-4(R)-(7-chloroquinoline-4-oxo)proline (5):

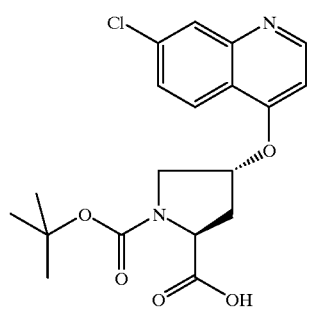

Commercially available Boc-4(S)-hydroxyproline methyl ester (500 mg, 2.04 mmol) and 7-chloro-4-hydroxyquinoline (440 mg, 2.45 mmol) were placed in dry THF (10 mL) at 0° C. Triphenylphosphine (641 mg, 2.95 mmol) was added, followed by slow addition of DIAD (426 mg, 2.45 mmol). The mixture was stirred at RT for 20 h. The reaction mixture was then concentrated, taken up in ethyl acetate and extracted three times with HCl 1N. The aqueous phase was basified with $Na_2CO_3$ and extracted twice with ethyl acetate. The organic layers were combined, dried over $MgSO_4$, filtered and concentrated to give a yellow oil. The oil was purified by flash chromatography to give compound (5) methyl ester as a white solid, 498 mg, 58% yield.

This methyl ester (400 mg, 0.986 mmol) was hydrolysed with 1M aqueous sodium hydroxide (1.7 mL, 1.7 mmol) in methanol (4 mL), at 0° C., for 3 h. The solution was concentrated to remove the methanol and neutralised with 1M aqueous HCl. The suspension was concentrated to dryness and taken up in methanol (20 mL), the salts were filtered off and the filtrate concentrated to give the desired compound (5) as a white solid, 387 mg, quant. yield.

$^1$H NMR (DMSO-$d_6$) (ca. 1:L mixture of rotamers) δ 8.74 (d, J=5 Hz, 1H), 8.13–8.09 (m, 1H), 7.99 and 7.98 (s, 1H), 7.58 (d, J=9 Hz, 1H), 7.02 (d, J=5 Hz, 1H), 5.26–5.20 (m, 1H), 4.10–4.01 (m, 1H), 3.81–3.72 (m, 1H), 3.59 (dd, J=12, 10 Hz, 1H), 2.41–2.31 (m, 2H), 1.34 and 1.31 (s, 9H).

Example 6
General procedure for coupling reactions done on solid support.

The synthesis was done on a parallel synthesizer model ACT396 from Advanced ChemTech® with the 96 well block. Typically, 24 peptides were synthesized in parallel using standard solid-phase techniques. The starting Fmoc-Nva-Wang resin and the 1-(Fmoc-amino)cyclopropane carboxylic acid-Wang resin were prepared by the DCC/DMAP coupling method (Atherton, E; Scheppard, R. C. *Solid Phase Peptide Synthesis, a Practical Approach*; IRL Press: Oxford 1989; pp 131–148). Other amino acid-Wang resins were obtained from commercial sources.

Each well was loaded with 100 mg of the starting resin (approximately 0.05 mmol). The resins were washed successively with 1.5 mL portions of NMP (1×) and DMF (3×). The Fmoc protecting group was removed by treatment with 1.5 mL of a 25% v/v solution of piperidine in DMF for 20 min. The resins were washed with 1.5 mL portions of DMF (4×), MeOH (3×) and DMF (3×). The coupling was done in DMF (350 μL), using 400 μL (0.2 mmol) of a 0.5M solution of Fmoc-amino acid/HOBt hydrate in DMF, 400 μL (0.4 mmol) of a 0.5M solution of DIPEA in DMF and 400 μL (0.2 mmol) of a 0.5M solution of TBTU in DMF. After shaking for 1 h, the wells were drained, the resins were washed with 1.5 mL of DMF and the coupling was repeated once more under the same conditions. The resins were then washed as described above and the cycle was repeated with the next amino acid.

The capping groups were introduced in two ways:
1. In the form of a carboxylic acid using the protocol described above (for example acetic acid) or,
2. As an acylating agent such as an anhydride or an acid chloride. The following example illustrates the capping with succinic anhydride: After the Fmoc deprotection and subsequent washing protocol, DMF was added (350 μL), followed by 400 μL each of a DMF solution of succinic anhydride (0.5 M, 0.2 mmol) and DIPEA (1.0 M, 0.4 mmol). The resins were stirred for 2 h and a recoupling step was performed.

At the end of the synthesis the resin was washed with 1.5 mL portions of DCM (3×), MeOH (3×), DCM (3×), and were dried under vacuum for 2 h.

The cleavage from the resin and concomitant side chain deprotection was effected by the addition of 1.5 mL of a mixture of TFA, $H_2O$, DTT and TIS (92.5:2.5:2.5:2.5). After shaking for 2.5 h, the resin was filtered and washed with 1.5 mL of DCM. The filtrates were combined and concentrated by vacuum centrifugation.

Each compound was purified by preparative reversed phase HPLC using a $C_{18}$ column (22 mm by 500 mm). The product-containing fractions were identified by MALDI-TOF mass spectrometry, combined and lyophilized.

Example 7

General procedure for coupling reactions done in solution {See also R. Knorr et al., Tetrahedron Letters, (1989), 30, 1927.}

The reactants, i.e. a free amine (1 eq.) (or its hydrochloride salt) and the free carboxylic acid (1 eq.) were dissolved in $CH_2Cl_2$, $CH_3CN$ or DMF. Under a nitrogen atmosphere, four equivalents of N-methylmorpholine and 1.05 equivalents of the coupling agent were added to the stirred solution. After 20 min, one equivalent of the second reactant, i.e. a free carboxylic acid was added. (Practical and efficient coupling reagents for this purpose are (benzotriazol-1-yloxy)tris-(dimethylamino)phosphonium hexafluorophosphate (HOFT) or preferably 2-(1H-benzotriazol-1-yl)-N,N,N',N'-tetramethyluronium tetrafluoroborate (TBTU) or O-(7-azabenzotriazol-1-yl)-N,N,N',N'-tetramethyluronium tetrafluoroborate (HATU). The reaction is monitored by TLC. After completion of the reaction, the solvent was evaporated under reduced pressure. The residue was dissolved in EtOAc. The solution was washed successively with 10% aqueous citric acid, saturated aqueous $NaHCO_3$ and brine. The organic phase was dried ($MgSO_4$), filtered and concentrated under reduced pressure. When the residue was purified, it was done by flash chromatography as defined above.

Example 8

Synthesis of segment: Ac-Chg-Chg-Pro (4(R)-naphthalen-1-ylmethoxy)—OH (8g)

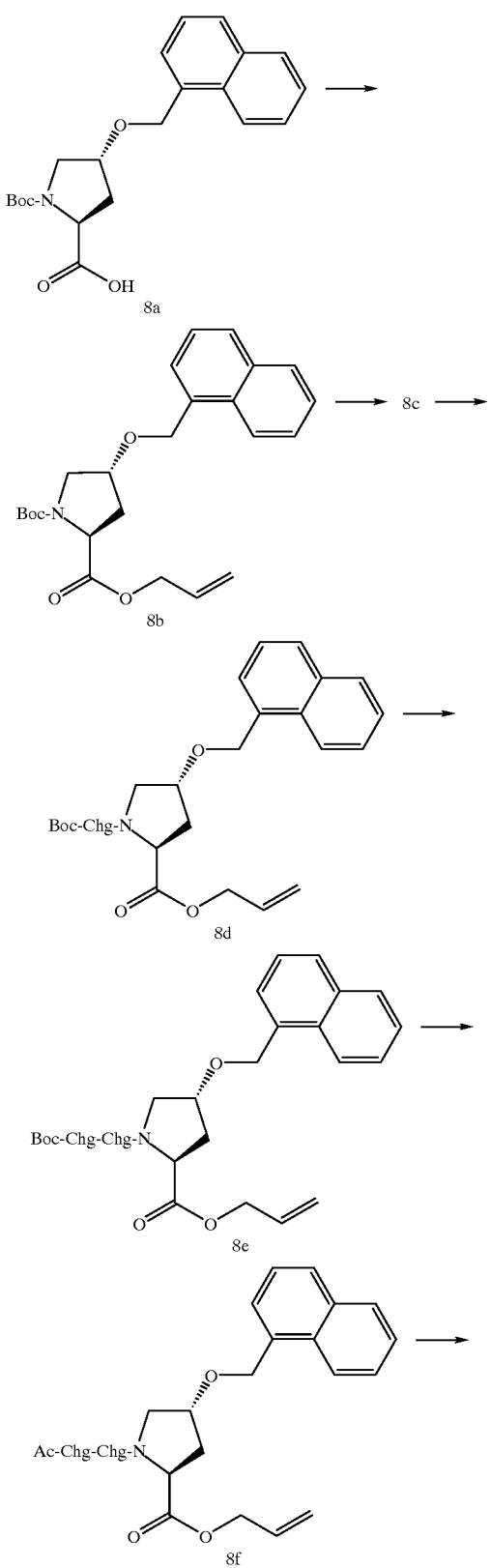

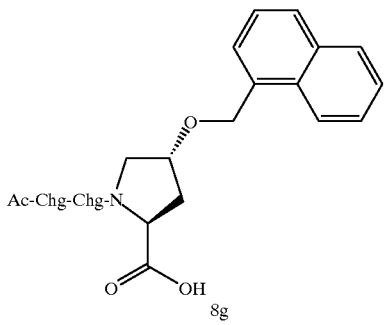

Compound 8a (4.45g, 11.98 mmol) was dissolved in anhydrous $CH_3CN$ (60 mL). DBU (2.2 mL, 14.38 mmol) and allyl bromide (1.1 mL, 13.18 mmol) were added successively and the reaction mixture was stirred 24 h at RT. The mixture was concentrated, the resulting oil was diluted with EtOAc and water and successively washed with water (2×) and brine (1×). The EtOAc layer was dried ($MgSO_4$), filtered and evaporated to dryness. The yellow oil was purified by flash chromatography (eluent:hexane:EtOAc;90:10 to 85:15) to provide the product 8b as a yellow oil (2, 4.17 g 85% yield ). MS (FAB) 412 $MH^+$ $^1H$ NMR ($CDCl_3$), mixture of rotamers ca.1:2, δ (d, J=8 Hz, 1H), 7.87 (d, J=8 Hz, 1H), 7.82 (d, J=8 Hz, 1H), 7.55–7.41 (m, 4H), 5.95–5.85 (m, 1H), 5.34–5.21 (m, 2H), 5.03–4.88 (m, 2H), 4.70–4.56 (m, 2H), 4.48 & 4.39 (t, J=8, 15 Hz, 1H) 4.28–4.23 (m, 1H), 3.81–3.55 (m, 2H), 2.46–2.36 (m, 1H), 2.13–2.05 (m, 1H), 1.44 & 1.41 (s, 9H).

Compound 8b (2.08 g , 5.05 mmol) was treated for 30 min at RT with 4N HCl/dioxane. Evaporation to dryness provided the corresponding amine-HCl as an oil. The amine-HCl 8c was dissolved in anhydrous DCM (25 mL), NMM (2.2 mL, 20.22 mmol), Boc-Chg-OH.$H_2O$ (1.53 g, 5.56 mmol) and TBTU (1.95 g, 6.07 mmol) were added successively. The reaction mixture was stirred at RT overnight, then, diluted with EtOAc and successively washed with 10% aqueous citric acid (2×), saturated aqueous $NaHCO_3$ (2×), water (2×), and brine (1×). The EtOAc layer was dried ($MgSO_4$), filtered and evaporated to dryness to provide the crude product 8d as a yellowish-white foam (ca 2.78g, 100% yield). MS (FAB) 551.4 $MH^+$. $^1H$ NMR ($CDCl_3$) δ 8.03(d, J=8 Hz, 1H), 7.86 (b d, J=8.5 Hz, 1H), 7.84 (d, J=8 Hz, 1H), 7.56–7.40 (m, 4H), 5.92–5.85 (m, 1H), 5.31 (dd, J=1, 17 Hz, 1H), 5.22 (dd, J=1, 10 Hz, 1H), 5.17 (d, J=9 Hz, 1H), 5.05 (d, J=12 Hz, 1H), 4.91 (d, J=12 Hz, 1H), 4.67–4.60 (m, 3H), 4.31–4.27 (m, 2H), 4.16 (b d, J=11 Hz, 1H), 3.71 (dd, J=4, 11 Hz, 1H), 2.47–2.41 (m, 1H), 2.08–1.99 (m,1H), 1.85–1.63 (m, 5H), 1.44–1.40 (m, 1H), 1.36 (s, 9H), 1.28–1.00 (m, 5H).

The crude dipeptide 8d (ca. 5.05 mmol) was treated with 4N HCl/dioxane (25 mL) as described for compound 8c. The crude hydrochloride salt was coupled to Boc-Chg-OH. $H_2O$ (1.53 g, 5.55 mmol) with NMM (2.22 mL, 20.22 mmol) and TBTU (1.95 g, 6.07 mmol) in DCM (25 mL) as described for compound 8d to yield crude tripeptide as a yellow-oil foam. The crude material was purified by flash chromatography (eluent:hexane:EtOAc;80:20 to 75:25) to provide the tripeptide 8e as a white foam (2.75 g; 79% yield over 2 steps). MS (FAB) 690.5 $MH^+$. $^1H$ NMR ($CDCl_3$), mainly one rotamer, δ 8.06 (d, J=8 Hz, 1H), 7.87 (b d, J=8.5 Hz, 1H), 7.82 (d, J=8 Hz, 1H), 7.57–7.40 (m, 4H), 6.41 (d, J=8.5 Hz, 1H), 5.92–5.84 (m, 1H), 5.31 (dd, J=1, 17 Hz, 1H), 5.23 (dd, J=1, 10.5 Hz, 1H), 5.04 (d, J=12 Hz, 1H), 4.98 (b d, J=7 Hz, 1H), 4.93 (d, J=12 Hz, 1H), 4.63–4.58 (m, 4H), 4.29–4.25 (m, 1H), 4.10–4.07 (m, 1H), 3.90–3.84 (m, 1H), 3.72 (dd, J=4, 11 Hz, 1H), 2.48–2.40 (m, 1H), 2.07–1.99 (m, 1H), 1.83–1.55 (m, 12H), 1.43 (s, 9H), 1. 23–0.89 (m, 1H)

The tripeptide 8e (2.75 g, 3.99 mmol) was treated with 4N HCl/dioxane (20 mL) as described for compound 8c. The crude hydrochloride salt was dissolved in anhydrous DCM (20 mL). MM (1.75 mL, 15.94 mmol) and acetic anhydride (752 µL, 7.97 mmol) were added successively. The reaction mixture was stirred overnight at RT, then diluted with EtOAc. The organic layer was washed successively with 10% aqueous citric acid (2×), saturated aqueous NaHCO$_3$ (2×), water (2×) and brine (1×), dried (MgSO$_4$), filtered, and evaporated to dryness to provide the crude tripeptide 8f as a white foam (2.48 g, 98% yield). MS (FAB) 632.4 MH$^{+1}$. $^1$H NMR (CDCl$_3$), mainly one rotamer, δ 8.06(b d, J=8 Hz, 1H), 7.87 (b d, J=8 Hz, 1H), 7.83 (d, J=8 Hz, 1H), 7.58–7.40 (m, 4H), 6.36 (d, J=9 Hz, 1H), 6.01 (d, J=9 Hz, 1H), 5.94–5.83 (m, 1H), 5.34–5.28 (m, 1H), 5.25–5.21 (m, 1H), 5.05 (d, J=12 Hz, 1H), 4.94 (d, J=12 Hz, 1H), 4.64–4.57 (m, 4H), 4.30–4.23 (m, 2H), 4.12–4.08 (m, 1H), 3.73 (dd, J=4, 11 Hz, 1H), 2.49–2.42 (m, 1H), 2.08–2.01 (m, 1H), 1.99 (s, 3H), 1.85–1.53 (m, 11H), 1.25–0.88 (m, 11H).

The crude tripeptide 8f (2.48 g, 3.93 mmol) was dissolved in an anhydrous mixture of CH$_3$CN: DCM (20 mL). Triphenylphosphine (53.5 mg, 0.200 mmol) and tetrakis(triphenylphosphine)-palladium (0) catalyst (117.9 mg, 0.102 mmol) were added successively, followed by pyrrolidine (353.9 µL, 4.24 mmol). The reaction mixture was stirred at RT for 18 h. Thereafter, the solvent was evaporated. The residue was dissolved in EtOAc and 10% aqueous citric acid then, further washes twice more with 10% aqueous citric acid, water (2×), and brine (1×). The organic layer was dried (MgSO$_4$), filtered and evaporated. The crude product was triturated in Et$_2$O: DCM (85:15) to provide after filtration the tripeptide 8g as a white solid (2.09 g, 90% yield). MS (FAB) 592.4 MH$^+$ 614.3 (M+Na)$^+$. $^1$H NMR (CDCl$_3$), mainly one rotamer, δ 8.08 (d, J=8 Hz, 1H), 7.93 (b d, J=9 Hz, 1H), 7.88 (b d, J=8 Hz, 1H), 7.82 (d, J=8 Hz, 1H), 7.57–7.41 (m, 4H), 6.47 (d, J=8.5 Hz, 1H), 5.05 (d, J=12.5 Hz, 1H), 4.94 (d, J=12.5 Hz, 1H), 4.73 (t, J=9.5, 19 Hz, 1H), 4.44–4.35 (m, 2H), 4.26 (b s, 1H), 4.19 (d, J=11.5 Hz, 1H), 3.75 (dd, J=4, 11 Hz, 1H), 2.47 (b dd, J=7.5, 13.5 Hz, 1H), 2.20–2.11 (m, 1H), 2.04 (s, 3H), 1.88–1.41 (m, 11H), 1.30–0.80 (11H).

Example 9

Synthesis of segment: Ac-Chg-Val-Pro(4(R)-naphthalen-1-ylmethoxy)-OH (9e)

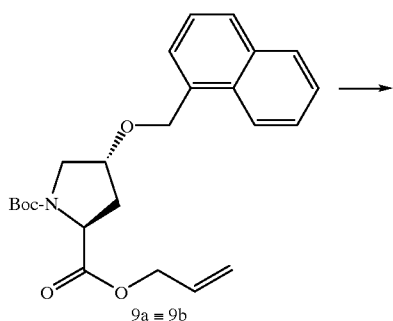

9a ≡ 9b

-continued

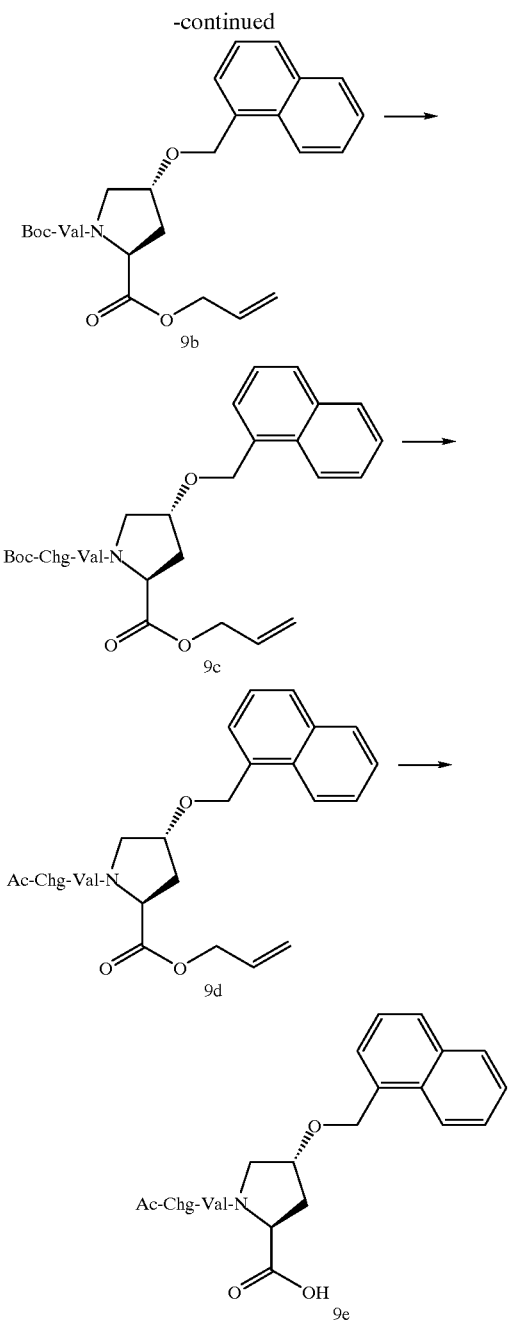

Compound 9a (2.89 g, 7.02 mmol) was treated with 4N HCl/dioxane (30 mL) as described for compound 8c. The crude hydrochloride salt was coupled to Boc-Val-OH (1.53 g, 7.73 mmol) with NMM (3.1 mL, 28.09 mmol) and TBTU (2.71 g, 8.43 mmol) in DCM (35 mL) for 3.5 h as described for compound 3 to provide the crude dipeptide 9b as an ivory oil-foam (ca.3.60 g, 100% yield). MS (FAB) 509.3 MH$^-$ 511.3 MH$^+$ 533.2 (M+Na)$^+$. $^1$H NMR (CDCl$_3$) δ 8.04 (b d, J=8 Hz, 1H), 7.87 (b d, J=7 Hz, 1H), 7.82 (d, J=8 Hz, 1H), 7.56–7.40 (m, 4H), 5.93–5.85 (m, 1H), 5.34–5.28 (m, 1H), 5.24–5.19 (m, 2H), 5.04 (d, J=12 Hz, 1H), 4.92 (d, J=12 Hz, 1H), 4.67–4.60 (m, 3H), 4.31–4.26 (m, 2H), 4.11–4.09 (m, 1H), 3.72 (dd, J=4, 11 Hz, 1H), 2.48–2.41 (mn, 1H), 2.07–1.99 (m, 1H), 1.44–1.36 (m, 1H), 1.37 (s, 9H), 1.01 (d, J=7 Hz, 3H), 0.93 (d, J=7 Hz, 3H).

The crude dipeptide 9b (ca. 7.02 mmol) was treated with 4N HCl/dioxane (30 mL) as described for compound 7c. The crude hydrochloride salt was coupled to Boc-Chg-OH. H$_2$O (2.13 g, 7.73 mmol) with NMM (3.1 mL, 28.09 mmol) and TBTU (2.71 g, 8.43 mmol) in CH$_2$Cl$_2$ (35 mL) as described for compound 3 to provide the crude tripeptide 9c as an ivory foam (ca.4.6 g, 100% yield). MS (FAB) 648.5 MH$^-$ 672.4 (M+Na)$^+$. $^1$H NMR (CDCl$_3$) δ 8.06 (b d, J=8 Hz, 1H), 7.87 (b d, J=7.5 Hz, 1H), 7.82 (b d , J=8 Hz, 1H), 7.57–7.40 (m, 4H), 6.46 (b d, J=8.5 Hz, 1H), 5.94–5.84 (m, 1H), 5.31 (dd, J=1, 17 Hz, 1H), 5.23 (dd, J=1, 10.5 Hz, 1H), 5.03 (d, J=12 Hz, 1H), 5.00–4.97 (m, 1H), 4.93 (d, J=, 12 Hz, 1H), 4.63–4.59 (m, 4H), 4.29–4.27 (m, 1H), 4.10–4.07 (m, 1H), 3.92–3.86 (m, 1H), 3.72 (dd, J=5, 11 Hz, 1H), 2.48–2.41 (m, 1H), 2.10–1.99 (m, 1H), 1.76–1.57 (m, 6H), 1.43 (s, 9H), 1.20–0.92 (m, 6H), 1.00 (d, J=7 Hz, 3H), 0.93 (d, J=7 Hz, 3H).

The crude tripeptide 9c (ca.7.02 mmol) was treated with 4N HCl/dioxane (30 mL) as described for compound 8c. The crude hydrochloride salt was further treated with acetic anhydride (1.33 mL, 14.05 mmol) and NMM (3.1 mL, 28.09 mmol) in CH$_2$Cl$_2$ (35 mL) as described for compound 8f. The crude product was flash purified (eluent:hexane:EtOAc;30:70) to provide the acetylated protected tripeptide 9d as a white foam (3.39 g, 81% yield over, steps). MS (FAB) 590.3 MH$^-$ 592.4 MH$^+$ 614.4 (M+Na)$^+$ $^1$H NMR (CDCl$_3$), mainly one rotamer, δ 8.06 (d, J=8 Hz, 1H), 7.88 (b d, J=8 Hz, 1H), 7.83 (d, J=8 Hz, 1H), 7.58–7.41 (m, 4H), 6.37 (d, J=9 Hz, 1H), 5.97 (d, J=8.5 Hz, 1H), 5.94–5.84 (m, 1H), 5.31 (dd, J=1, 17 Hz, 1H), 5.24 (dd, J=1, 10.5 Hz, 1H), 5.05 (d, J=12 Hz, 1H), 4.94 (d, J=12 Hz, 1H), 4.66–4.57 (m, 4H), 4.31–4.22 (m, 2H), 4.11–4.05 (m, 1H), 3.73 (dd, J=4.5, 11 Hz, 1H), 2.50–2.43 (m, 1H), 2.09–2.01 (m, 2H), 2.00 (s, 3H), 1.68–1.55 (m, 5H), 1.15–0.89 (m, 6H), 0.99 (d, J=7 Hz, 3H), 0.91 (d, J=7 Hz, 3H).

The acetylated tripeptide 9d (3.39 g, 5.73 mmol) was deprotected by tetrakis(triphenylphosphine)-palladium (0) catalyst (172.1 mg, 0.149 mmol) with triphenylphosphine (78.1 mg, 0.298 mmol) and pyrrolidine (516 μL, 6.19 mmol) in a 1:1 mixture of anhydrous CH$_3$CN: DCM (30 mL) as described for compound 8g. The crude light yellow foam product was triturated in Et$_2$O: DCM (85:15)to provide after filtration the tripeptide 9e as an off-white solid (3.0 g; 95% yield). MS (FAB) 550.3 MH$^-$ $^1$H NMR (CDCl$_3$) δ 8.08 (d, J=8 Hz, 1H), 8.04 (b d, J=9 Hz, 1H), 7.88 (b d, J=7.5 Hz, 1H), 7.82 (d, J=8 Hz, 1H), 7.58–7.37 (m, 5H), 5.05 (d, J=12 Hz, 1H), 4.94 (d, J=12 Hz, 1H), 4.61 (t, J=9.5, 19.5 Hz, 1H), 4.46–4.37 (m, 2H), 4.27 (b s, 1H), 4.17 (d, J=11 Hz, 1H), 3.74 (dd, J=4, 11 Hz, 1H), 2.49 (b dd, J=7.5, 13 Hz, 1H), 2.17–2.09 (m, 1H), 2.04 (s, 3H), 2.03–1.94 (m, 1H), 1.79 (b d, J=12.5 Hz, 1H), 1.62–1.43 (m, 5H), 1.08–0.85 (m, 5H), 1.00 (d, J=7 Hz, 3H), 0.90 (d, J=7 Hz, 3H).

Example 10

Synthesis of pentapeptide 10h:

The synthesis was done as follows:

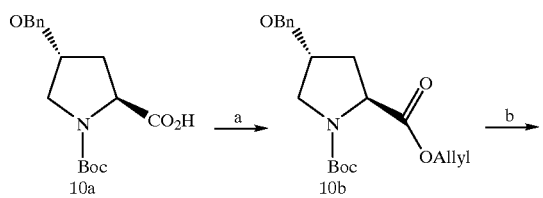

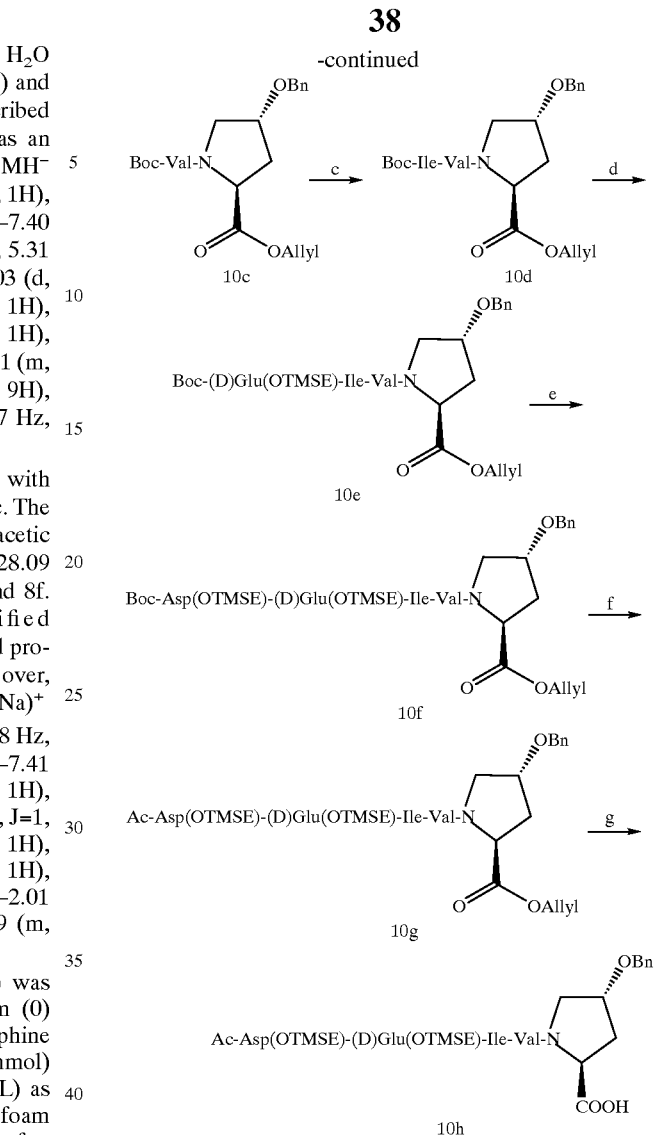

a) Synthesis of compound 10b:

To a solution of commercially available Boc-4(R)-benzyloxyproline (10a) (20.0 g, 62.2 mmol) in acetonitrile (250 mL) at 0° C. were successively added DBU (10.3 mL, 68.87 mmol) and allyl bromide (6.0 mL, 69.3 mmol). The reaction mixture was stirred overnight at RT, then the acetonitrile was evaporated and the residue dissolved in EtOAc. The mixture was sequentially washed with 10% aqueous citric acid (2×), water, saturated aqueous NaHCO$_3$, water (2×) and brine. The EtOAc solution was dried (MgSO$_4$), filtered and concentrated to afford the desired ester 10b (21.84 g, 60.42 mmol, 97% yield) as a colourless oil.

b) Synthesis of compound 10c:

Allyl ester 10b (21.84 g, 60.42 mmol) was treated with a 4 N HCl solution in dioxane (453 mL, 1812.0 mmol) for 30 min before being concentrated in vacuo. The amine hydrochloride was subjected to the reaction conditions described in Example 3: The crude hydrochloride salt was combined with Boc-Val-OH (13.13 g, 60.43 mmol), NMM (26.6 mL, 241.93 mmol), and TBTU (23.3 g, 72.56 mmol) in CH$_2$Cl$_2$ (300 mL). The reaction mixture was stirred for 16 h at RT and then concentrated in vacuo. The residue was dissolved in EtOAc and washed sequentially with 10% aqueous citric acid (2×), water, saturated aqueous NaHCO$_3$ (2×), water (2×), and brine. The organic layer was dried (MgSO$_4$), filtered and concentrated to afford the crude dipeptide 10c (30.23 g). MS (FAB) 461 (MH$^+$). $^1$H-NMR (CDCl$_3$) δ 7.36–7.28 (m, 5H), 5.91–5.84 (m, 1H), 5.35–5.21 (m, 2H), 5.19 (bs, 1H), 4.66–4.62 (m, 3H), 4.56 (d, J=11.8 Hz, 1H), 4.49 (d, J=11.4 Hz, 1H), 4.28–4.24 (m, 2H), 4.04 (bd, J=11.1 Hz, 1H), 3.70 (dd, J=4.5, 11.1 Hz, 1H), 2.25–2.42 (m, 1H), 2.08–1.98 (m, 1H), 1.45–1.40 (m, 1H), 1.41 (s, 9H), 1.01 (d, J=6.7 Hz, 3H), 0.93 (d, J=6.7 Hz, 3H).

c) Synthesis of compound 10d:

The crude dipeptide 10c (ca. 60 mmol) was treated with a 4 N HCl in dioxane solution (453 mL). The crude hydrochloride salt was combined with Boc-Ile-OH (14.0 g, 60.5 mmol), TBTU (23.3g, 72.6 mmol) and NMM (26.6 mL, 241.9 mmol, 4.0 eq.) in CH$_2$Cl$_2$ (300 mL) as described for compound 10c to afford the crude tripeptide 10d. Purification by flash chromatography (using a mixture of 30% EtOAc in hexane) gave the desired compound 10d (25.61 g, 44.64 mmol, 72% yield from compound 10a). MS (FAB) 574 (MH$^+$); $^1$H-NMR (CDCl$_3$) δ 7.37–7.28 (m, 5H), 6.44 (d, J=8.6 Hz, 1H), 5.95–5.84 (m, 1H), 5.35–5.23 (m, 2H), 5.99(d, J=8.4 Hz, 1H), 4.65–4.47 (m, 3H), 4.56 (d, J=11.8 Hz, 1H), 4.49 (d, J=12.1 Hz, 1H), 4.27–4.21 (m, 1H), 4.03 (bd, J=10.8 Hz, 1H), 3.97–3.88 (m, 1H), 3.71 (dd, J=4.1 Hz, J=10.8 Hz, 1H), 2.49–2.41 (m, 1H), 2.12–2.00 (m, 2H), 1.85–1.74 (m, 1H), 1.55–1.40 (m, 2H), 1.43 (s, 9H), 1.16–1.04 (m, 1H), 1.00 (d, J=6.7 Hz, 3H), 0.93 (d, J=6.7 Hz, 3H), 0.89–0.82 (m, 6H).

d) Synthesis of compound 10e:

Tripeptide 10d (25.60 g; 44.62 mmol) was treated with a 4 N HCl in dioxane solution (30 min) before being concentrated in vacuo to give 22.64 g of the hydrochloride salt. The hydrochloride salt (14.97 g, 29.35 mmol) was combined with Boc-(D)Glu(OTMSE)-OH (10.2 g, 29.35 mmol), TBTU (11.30 g, 35.23 mmol) and NMM (11.30 g, 35.23 mmol) in CH$_2$Cl$_2$ (150 mL) as described for compound 10c. Compound 10e was obtained as an off-white foam (23.6 g). MS (FAB) 803.5 (MH$^+$); $^1$H-NMR (CDCl$_3$) δ 7.34–7.28 (m, 5H), 6.74 (d, J=8.26 Hz, 1H), 6.49 (d, J=8.90 Hz, 1H), 5.93–5.86 (m, 1H), 5.44–5.36 (m, 1H), 5.35–5.22 (m, 2H), 4.64–4.48 (m, 6H), 4.27–4.15 (m, 4H), 4.02 (d, J=11.13 Hz, 1H), 3.71 (dd, J=11.13, 4.45 Hz, 2H), 2.49–2.41(m, 2H), 2.40–2.34 (m, 1H), 2.18–2.00 (m, 3H), 1.96–1.71 (m, 2H), 1.50–1.40 (m, 1H), 1.43 (s, 9H), 1.15–1.04 (m, 1H), 1.02–0.95 (m, 1H), 0.97 (d, J=8.27 Hz, 3H), 0.90 (d, J=7.00 Hz, 3H), 0.87–0.82 (m, 1H), 0.84 (d, J=6.67 Hz, 6H), 0.04 (s, 9H).

e) Synthesis of compound 10f:

The crude tetrapeptide 10e (ca. 28.91 mmol) was treated with a 4 N HCl in dioxane solution for 30 min (150 mL). The crude hydrochloride salt was combined with Boc-Asp (OTMSE)-OH (10.15 g, 30.44 mmol), NMM (12.7 mL, 115.6 mmol), and TBTU (11.14 g, 34.70 mmol) in CH$_2$Cl$_2$ (150 mL) as described for compound 10c. Pentapeptide 10f was obtained as a light yellow foam (ca. 29.5 g). MS (FAB) 1018 (MH$^+$); $^1$H-NMR (CDCl$_3$) δ 7.36–7.28 (m, 6H), 6.78 (d, J=8.90 Hz, 1H), 6.72 (d, J=8.58 Hz, 1H), 6.22 (d, J=7.94 Hz, 1H), 5.93–5.83 (m, 1H), 5.33–5.21 (m, 2H), 4.62–4.57 (m, 6H), 4.49–4.36 (m, 2H), 4.30 (dd, J=8.90, 6.35 Hz, 1H), 4.23–4.14 (m, 5H), 3.72 (dd, J=11.13, 4.77 Hz, 2H), 2.89 (dd, J=16.85, 6.36 Hz, 1H), 2.79 (dd, J=16.85, 6.36 Hz, 1H), 2.48–2.27 (m, 3H), 2.21–1.94 (m, 5H), 1.46–1.42 (m, 1H), 1.45 (s, 9H), 1.17–1.07 (m, 1H), 1.00–0.86 (m, 4H), 0.99 (d, J=6.68 Hz, 3H) 0.93 (d, J=6.68 Hz, 3H), 0.90 (d, J=6.67 Hz, 6H), 0.04 (s, 9H), 0.02 (s, 9H).

f) Synthesis of compound 10g:

The Boc-pentapeptide 10f (ca. 28.91 mmol) was treated with a 4 N HCl in dioxane solution (150 mL) for 30 min before being concentrated in vacuo. The crude hydrochloride salt was dissolved in anhydrous DMF (150 mL) followed by the successive addition of pyridine (51.4 mL, 636.2 mmol) and acetic anhydride (51.6 mL, 546.5 mmol). The reaction mixture was stirred overnight at RT then poured into brine and extracted with EtOAc (3×). The combined organic extracts were washed sequentially with 10% aqueous citric acid (2×), saturated NaHCO$_3$ (2×), water (2×) and brine (1×). The organic layer was dried (MgSO$_4$), filtered and evaporated to dryness. The oil/foam residue was purified by flash chromatography (eluent, hexane:EtOAc; 4:6) to provide the acetylated pentapeptide 10g as a white amorphous solid (17.56 g, 63% yield from compound 10d). MS (FAB) 960.7 (MH$^+$) 982.9 (MNa$^+$); $^1$H-NMR (CDCl$_3$) δ 7.72 (d, J=9.22 Hz, 1H), 7.35–7.28 (m, 6H), 7.12 (d, J=9.54 Hz, 1H) 6.63 (d , J=8.26 Hz, 1H), 5.91–5.81 (m, 1H), 5.32–5.22 (m, 2H), 5.20–4.96 (m, 1H), 4.68–4.54 (m, 5H), 4.49–4.36 (m, 3H), 4.28–4.20 (m, 3H), 4.19–4.12 (m, 2H), 3.74 (dd , J=11.76, 5.40 Hz , 2H), 2.93 (dd, J=17.48, 4.45 Hz, 1H), 2.81 (dd, J=17.49, 6.36 Hz, 1H), 2.47–2.39 (m, 2H), 2.33–2.24 (m, 1H), 2.14–1.95 (m, 5H), 2.03 (s, 3H), 1.52–1.42 (m, 1H), 1.17–1.07 (m, 1H), 1.02–0.88 (m, 16H), 0.04 (s, 9H), 0.03 (s, 9H).

g) Synthesis of compound 10h:

The pentapeptide 10g (16.01 g, 16.67 mmol) was suspended in anhydrous acetonitrile (100 mL) and treated successively with triphenylphosphine (227.4 mg, 0.87 mmol) and tetrakis(triphenylphosphine)-palladium (0) catalyst (501 mg, 0.433 mmol) followed by pyrrolidine (1.5 mL, 18.01 mmol). The reaction mixture was mechanically stirred for 4 h at RT and then concentrated in vacuo. The residue was dissolved in EtOAc and washed sequentially with 10% aqueous citric acid (3×), water (3×), and brine (1×). The organic phase was dried (MgSO$_4$), filtered and evaporated to dryness. The crude product was purified by flash chromatography (eluent, 1% HOAc, 2.3% MeOH in CHCl$_3$) to provide the pentapeptide 10h as a white amorphous solid (11.45 g, 75% yield). MS (FAB) 920 (MH$^+$), 942 (MNa$^+$), 958.6 (M+K); $^1$H-NMR (CDCl$_3$) δ 7.53(d, J=8.90 Hz, 1H), 7.40 (d, J=7.32 Hz, 1H), 7.35–7.28 (m, 5H), 7.22–7.17 (m, 1H), 6.83 (d, J=7.31 Hz, 1H) 5.00–4.94 (m, 1H), 4.64–4.61 (m, 2H), 4.53–4.44 (m, 3H), 4.35 (dd, J=8.26, 6.04 Hz, 1H), 4.28–4.24 (m, 1H), 4.18–4.09 (m, 5H), 3.72 (dd, J=10.81, 4.14 Hz, 1H), 2.87–2.84 (m , 2H), 2.47–2.41 (m, 2H), 2.34–2.24 (m, 1H), 2.16–1.97 (m, 5H), 2.06 (s, 3H), 1.52–1.42 (m, 1H), 1.17–1.08 (m, 1H), 1.01–0.84 (m, 16H), 0.04 (s, 9H), 0.03 (s, 9H).

Example 11
Synthesis of compound 102 (Table 1)

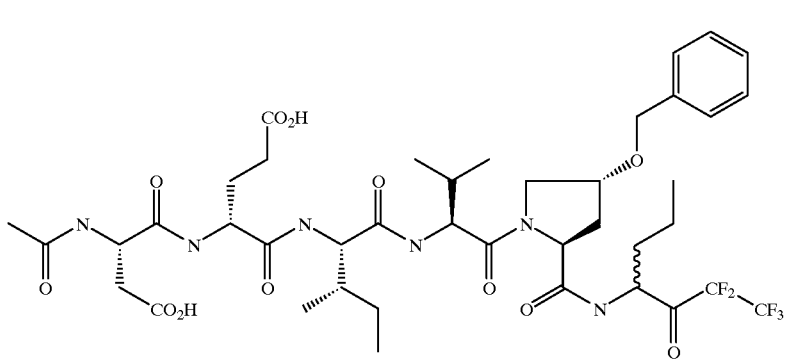

102

The synthesis was done as shown below:

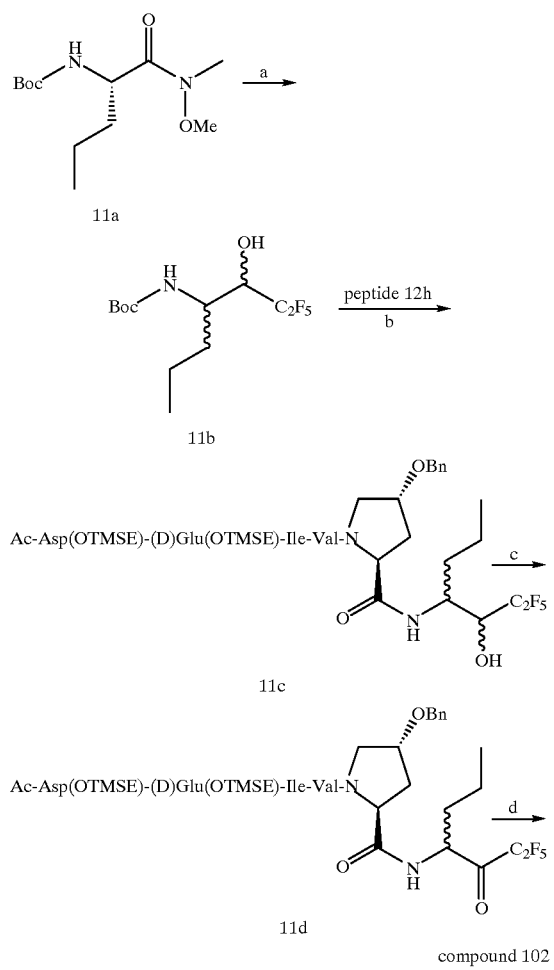

compound 102 a) Synthesis of compound 11b:

A cold (−78° C.) solution of commercially available pentafluoroethyl iodide (6.4 g, 26.02 mmol) in dry ether (16.7 mL) was slowly canulated (10 min) into a −78° C. solution of MeLi.LiBr in ether (14.0 mL of a 1.5 M solution in ether, 21.0 mmol). After an additional 10 min at −78° C. Weinreb amide 11a (prepared from commercially available Boc-Nva-OH according to the procedure of Castro, B. et al. Synthesis, (1983), 676–678.)(2.02 g, 7.76 mmol) in ether (5 mL) was added. The reaction mixture was stirred for 1 hr at −78° C. and then at −40° C. for 15 min. A saturated aqueous solution of $NH_4Cl$ was then added. The mixture was extracted 3 times with EtOAc and the combined organic extract was washed with brine. The EtOAc solution was finally dried over $MgSO_4$, filtered and concentrated. The crude pentafluoroethyl ketone was dissolved in a mixture of THF (38 mL) and MeOH (9.5 mL) and the resulting solution was cooled to 0° C. for the addition of sodium borohydride (323 mg, 8.54 mmol, 1.1 eq.). After 15 min, ether was added and the mixture was washed with a 10% aqueous citric acid solution. The aqueous layer was extracted 3 times with ether and the combined organic layer was successively washed with a saturated aqueous $NaHCO_3$ solution (2x), water and brine. The ether solution was dried ($Na_2SO_4$) filtered and concentrated. The residue was flash chromatographed using a mixture of EtOAc (15%) and hexane (85%) to afford the desired alcohols (1.30 g, 4.05 mmol, 52% yield from the amide 11a). $^1H$ NMR ($CDCl_3$) (mixture of 2 diastereomers in a 1:1 ratio) δ 4.75 (bs, 1/2H), 4.54 (bs, 1/2H), 4.21–4.13 (m, 1H), 3.92 (dd, J=6.0 Hz, J'=14.6 Hz, 1H), 1.65–1.29 (m, 4H), 1.45 (m, 9H), 0.98–0.93 (m, 3H).

b) Synthesis of compound 11c:

Compound 11b (96 mg, 0.30 mmol) was treated with a 4 N HCl solution in dioxane for 30 min before being concentrated in vacuo. The crude hydrochloride salt was dissolved in dry DMF (1 mL). The pentapeptide 10h (204 mg, 0.22 mmol), NMM (0.1 mL, 0.91 mmol, 4 eq.)and TBTU (85 mg, 0.26 mmol, 1.2 eq.) were then successively added. The reaction mixture was stirred overnight at RT, then poured into brine and extracted 3 times with EtOAc. The combined organic extract was successively washed with a 10% aqueous citric acid solution (2x), water, saturated aqueous $NaHCO_3$ solution, water (2x) and brine. The EtOAc solution was dried ($MgSO_4$), filtered and concentrated. The residue was purified by flash chromatography using a mixture of EtOAc (75 to 80%) and hexane (25 to 20%) to afford the desired compound 11c (154 mg, 0.137 mmol, 62% yield). MS (FAB) 1123 ($MH^+$).

c) Synthesis of compound 11d:

To the mixture of alcohols 11c (52 mg, 0.047 mmol) in a solution of DMSO (0.5 mL) and toluene (0.5 mL) were successively added dichloroacetic acid (11.5 mL, 0.139 mmol) and EDAC (89 mg, 0.464 mmol). The reaction mixture was stirred overnight at RT, poured into brine (30 mL) and extracted with EtOAc (3x15 mL). The combined organic extract was successively washed with saturated aqueous $NaHCO_3$, water (2x) and brine. The EtOAc solution was dried (MgSO$_4$), filtered and concentrated. The residue was purified by flash chromatography using a mixture of EtOAc (75 to 80%) and hexane (25 to 20%) to afford the desired ketone 11d (37 mg, 0.032 mmol, 70% yield). MS (FAB) 1121 (MH$^+$).

d) Synthesis of compound 102:

The mixture of ketone lid (37 mg, 0.032 mmol) was dissolved in TFA (1 mL) and the resulting solution was stirred for 1 h at RT. After removal of the volatiles under vacuum, the desired peptide was obtained (29 mg, 0.031 mmol, 97%). MS (FAB) 921 (MH$^+$), 943 (MNa$^+$). $^1$H NMR (CDCl$_3$)(mixture of 2 diastereomers in a 1.35:1 ratio) d 8.14 (d, J=7.6 Hz, 1H), 8.07–8.02 (m, 2H), 7.80–7.78 (m, 1H), 7.35–7.26 (m, 5H), 4.77–4.56 (m, 1H), 4.56–4.38 (m, 5H), 4.34–4.09 (m, 5H), 2.68–2.59 (m, 2H), 2.26–2.15 (m, 3H), 2.02–1.82 (m, 3H), 1.82 (s, 3H), 1.78–1.28 (m, 6H), 1.07–0.95 (m, 1H), 0.92–0.80 (m, 10H), 0.77–0.68 (m, 8H).

Example 12

Synthesis of compound 205 (Table 2).

by analytical HPLC (97.5%). MS (FAB) 173.1 (MH$^+$); $^1$H-NMR (DMSO-d$_6$) d 10.33 (bs, 1H), 7.28 (bs, 1H), 2.19–2.09 (m, 2H), 1.42 and 1.41 (2×s, 9H), 0.97 (dt, J=7.6, 1.6 Hz, 3H).

b) Synthesis of compound 12b:

To the hydrazone 12a (3.7 g, 21.48 mmol) in THF (80 mL) at −78° C. was added DIBAL (31 mL, 47.25 mmol) as a 1.5 M solution in toluene. The reaction was maintained at −78° C. for 2 h and then −40° C. for 2 h. Rochelle's salt (aqueous potassium sodium tartrate) solution was added and the reaction mixture stirred at RT overnight. The organic phase was separated and the aqueous phase extracted with Et$_2$O (2×75 mL). The combined organic extracts were washed with brine, dried (Na$_2$SO$_4$), filtered and concentrated in vacuo. Purification by flash chromatography on silica gel gave 12b as a colourless oil (3.4 g, 91%). MS (CI—NH$_3$) 175.2 (MH$^+$); $^1$H-NMR (DMSO-d$_6$) d 8.10 (bs, 1H), 4.25 (bs, 1H), 2.6 (t, J=7.0 Hz, 2H), 1.45–1.29 (m, 2H), 1.38 (s, 9H), 0.85 (t, J=7.6 Hz, 3H).

c) Synthesis of compound 12c:

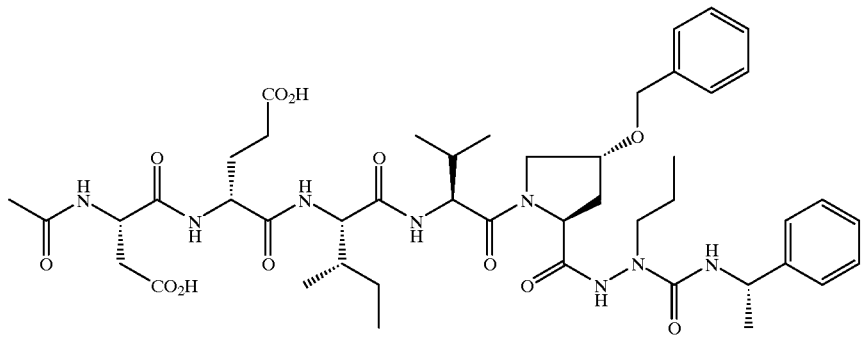

Compound 205 was prepared according to the following scheme:

The hydrazine 12b (0.20 g, 1.15 mmol) was combined with (S)-(−)-1-phenylethylisocyanate (0.162 g, 1.15 mmol)

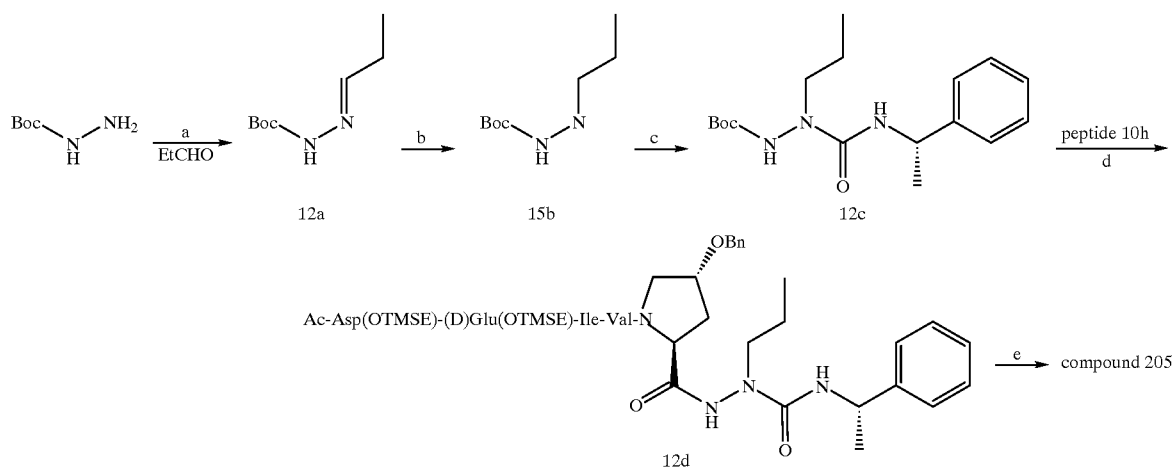

a) Synthesis of compound 12a:

To a solution of Boc-hydrazine (3.0 g, 22.6 mmol) in toluene (42 mL) was added propionaldehyde (1.8 mL, 24.9 mmol). The solution was heated to 50° C. for 1 h and then stirred at RT for 24 h. The mixture was concentrated to give 12a as a white solid (3.70 g, 95%) which was homogeneous in CH$_2$Cl$_2$ (2.4 mL) with DIPEA (0.44 mL, 2.52 mmol) and stirred at 0° C. for 1 h, and then at RT for 3 h. The mixture was concentrated in vacuo to give a white solid which was purified by flash chromatography to give compound 12c (0.25 g, 68%). MS (FAB) 322.3 (MH$^+$); $^1$H-NMR (DMSO-d$_6$) d 8.90 and 8.48 (2×bs, 1H), 7.35–7.23 (m, 5H), 6.84 (t, J=7.0 Hz, 1H), 6.50 (bs, 1H), 4.79 (t, J=7.3 Hz, 1H), 1.41 (s, 9H), 1.36 (d, J=7.0 Hz, 6H), 0.81 (t, J=7.3 Hz, 3H).

d) Synthesis of compound 12d:

Compound 12c (77 mg, 0.24 mmol) was treated with 4 N HCl/dioxane (1.2 mL) for 20 min before being concentrated in vacuo. The hydrochloride salt was combined with the pentapeptide 10h (0.20 g, 0.22 mmol), TBTU (85 mg, 0.26 mmol), and diisopropylethylamine (0.13 mL, 0.73 mmol) in DMF (2.5 mL) at RT for 16 h. The reaction mixture was concentrated and the residue dissolved in EtOAc and washed sequentially with saturated aqueous NaHCO$_3$, 10% aqueous HCl, and brine before being dried (MgSO$_4$), filtered, and concentrated in vacuo. Purification by flash chromatography gave 12d as a white solid (80 mg, 33%).

e) Synthesis of compound 205:

The protected peptide 12d (75 mg, 0.067 mmol) was treated with neat TFA (1.5 mL) for 1.5 h before being concentrated in vacuo. Purification by preparative HPLC gave 205 as a white solid (17 mg, 27%). HPLC (98%); MS (FAB) 923.6 (MH$^+$); HRMS calcd for C$_{46}$H$_{66}$N$_8$O$_{12}$ (MH$^+$) 923.48785, found: 923.49097. $^1$H-NMR (DMSO-d$_6$) d 12.5–11.9 (bs, 2H), 10.31 (bs, 1H), 8.26 (d, J=7.95 Hz, 1H), 8.14 (d, J=7.6 Hz, 1H), 7.98 (d, J=8.26 Hz, 1H), 7.78 (d, J=8.58 Hz, 1H), 7.42–7.26 (m, 10H), 7.20 (t, J=7.0 Hz, 1H), 6.86 (bd, 1H), 4.85–4.77 (m, 1H), 4.55 (d, J=11.4 Hz, 1H), 4.50–4.40 (m, 1H), 4.46 (d, J=11.8 Hz, 1H), 4.36–4.20 (m, 6H), 3.75–3.68 (m, 1H), 3.48–3.34 (bs, 1H), 3.18–3.07 (bs, 1H), 2.62 (dd, J=16.5, 5.7 Hz, 1H), 2.44 (dd, J=16.5, 5.7 Hz, 1H), 2.30–2.22 (m, 1H), 2.17 (t, J=7.95 Hz, 2H), 2.06–1.84 (m, 2H), 1.81 (s, 3H), 1.80–1.59 (m, 2H), 1.42–1.30 (m, 6H), 1.06–0.98 (m, 1H), 0.88 (t, J=7.0 Hz, 6H), 0.78 (t, J=7.3 Hz, 3H), 0.71 (t, J=7.0 Hz, 6H).

Example 13

Synthesis of compound 231

Compound 231 was prepared according to the procedure for compound 205 except that the isocyanate was replaced by the corresponding isocyanate prepared from piperonylamine in the following manner. To a solution of phosgene in toluene (0.2 mL, 0.38 mmol, 4 equiv.) and THF (0.7 mL) at 0° C. was added piperonylamine (12 μL, 0.095 mmol) in THF (0.7 mL) containing diisopropylethylamine (53 μL, 0.30 mmol) dropwise over a period of 15 min. The mixture was stirred at 0° C. for 30 min before being concentrated. The generated isocyanate was coupled as described for compound 12c. The Boc group was removed (4 N HCl/dioxane) and the hydrochloride salt of fragment P1/P1' was coupled in the usual fashion with HATU, diisopropylethylamine and the pentapeptide 10h (0.10 g, 0.095 mmol) in DMF. The reaction mixture was stirred at 0° C. for 1 h and then at RT for 16 h. The reaction mixture was concentrated and the residue dissolved in EtOAc and washed sequentially with saturated aqueous NaHCO$_3$, 10% aqueous HCl, and brine before being dried (MgSO$_4$), filtered and concentrated in vacuo. Purification by flash chromatography gave the desired protected peptide (67 mg, 62.5%).

The protected peptide (63 mg, 0.056 mmol) was treated as for the synthesis of compound 12d to give after purification by preparative HPLC compound 231 as a white solid (17 mg, 32%). HPLC (100%); MS (FAB) 953.05 (MH$^+$); HRMS calcd for C$_{46}$H$_{64}$N$_8$O$_{14}$ (MH$^+$) 953.46204, found: 953.46680. $^1$H-NMR (DMSO-d$_6$) δ 10.35 (bs, 1H), 8.17 (d, J=8.6 Hz, 1H), 8.15 (d, J=7.95 Hz, 1H), 7.98 (d, J=7.95 Hz, 1H), 7.76 (d, J=8.6 Hz, 1H), 7.40–7.25 (m, 5H), 7.23–7.13 (bs, 1H), 6.82 (s, 1H), 6.79 (d, J=7.6 Hz, 1H), 6.72 (d, J=7.6 Hz, 1H), 5.95 (s, 2H), 4.57–4.43 (m, 3H), 4.34–4.18 (m, 6H), 4.13–4.08 (m, 2H), 3.70 (d, J=3.8 Hz, 1H), 3.67 (d, J=3.8 Hz, 1H), 2.68–2.58 (m, 2H), 2.48–2.42 (m, 1H), 2.34–2.24 (m, 2H), 2.2–2.13 (m, 2H), 2.05–1.94 (m, 1H), 1.94–1.82 (m, 1H), 1.81 (s, 3H), 1.75–1.61 (m, 2H), 1.45–1.30 (m, 3H), 1.03–0.94 (m, 1H), 0.87–0.75 (m, 9H), 0.74–0.67 (m, 6H).

Example 14

Synthesis of compound 232

Compound 12b was coupled to the appropriate carboxylic acid (from Maybridge) using TBTU and diisopropylethylamine in DMF in the usual fashion. The Boc group from the P1/P1' fragment was removed (4 N HCl/dioxane, 30 min) and the corresponding hydrochloride salt (0.104 mmol) coupled to peptide 10h (0.10 g, 0.095 mmol) in the usual fashion with HATU (39.5 mg, 0.104 mmol) and diisopropylethylamine (0.07 mL, 0.4 mmol) in DMF (0.95 mL) for 16 h. The mixture was concentrated and the residue extracted into EtOAc and washed with saturated aqueous NaHCO$_3$, 10% aqueous HCl and brine before being dried (Na$_2$SO$_4$), filtered and concentrated in vacuo to give the protected peptide (110 mg, 100%). Final deprotection of this peptide was accomplished by saponification. The protected peptide (0.105 mg, 0.09 mmol) was dissolved in THF (1.3 mL), MeOH (0.7 mL) and H$_2$O (0.7 mL) before being treated with aqueous NaOH (0.18 mL of a 2 N solution, 0.36 mmol). The mixture was stirred for 3.5 h before being concentrated in vacuo. The crude residue was purified by preparative HPLC to give compound 232 as a white solid (33 mg, 36%). HPLC (97%); MS (FAB) 977.4 (MH$^+$), 999.4 (MNa$^+$); HRMS calcd for C$_{47}$H$_{64}$N$_{10}$O$_{13}$ (MH$^+$) 977.47327, found: 97747620. $^1$H-NMR (DMSO-d$_6$) δ 10.61 (bs, 1H), 8.75 (d, J=4.7 Hz, 1H), 8.14 (d, J=8.6 Hz, 1H), 8.06 (d, J=7.6 Hz, 1H), 8.02–7.90 (m, 3H), 7.87 (d, J=8.6 Hz, 1H), 7.60–7.56 (m, 1H), 7.35–7.26 (m, 5H), 4.57–4.43 (m, 4H), 4.42–4.34 (m, 2H), 4.33–4.25 (m, 2H), 4.25–4.17 (m, 2H), 3.70 (dd, J=10.5, 10.5 Hz, 1H), 3.21–3.10 (m, 2H), 2.96–2.80 (m, 1H), 2.69–2.60 (m, 2H), 2.48–2.41 (m, 1H), 2.35–2.25 (m, 1H), 2.22–2.15 (m, 2H), 2.05–1.90 (m, 2H), 1.88–1.81 (m, 1H), 1.80 (s, 3H), 1.77–1.61 (m, 2H), 1.53–1.40 (m, 2H), 1.39–1.28 (m, 1H), 1.06–0.95 (m, 1H), 0.91–0.81 (m, 7H), 0.79 (t, J=7.3 Hz, 3H), 0.75–0.67 (m, 6H).

Example 15

Synthesis of compound 233

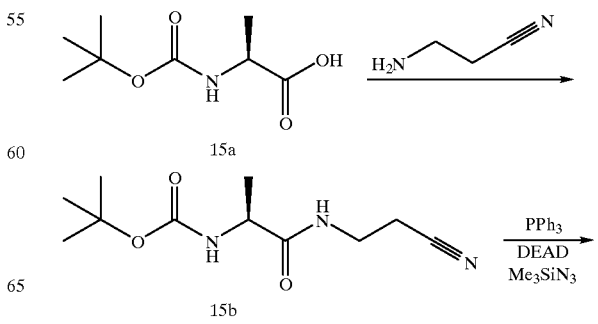

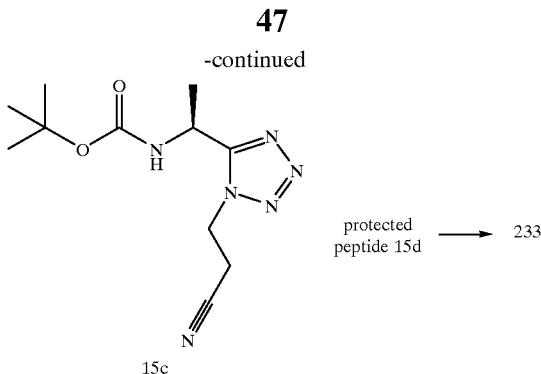

protected peptide 15d → 233

Synthesis of compound 15b:

Boc-Alanine (15a) (5 g, 265.42 mmol) was dissolved in anhydrous DMF (63 mL) at 0° C. before 3-aminopropionitrile (1.9 mL, 26.42 mmol) and HOBt (3.5 g, 26.42 mmol) were added. To this solution was added DCC (26.4 mL, 26.4 mmol, 1.0 M in dichloromethane) via syringe. The mixture was stirred at 0° C. for 24 h. The generated DCU was filtered out through a pad of Celite and washed with cold dichloromethane. The filtrate was concentrated in vacuo and the residue re-dissolved in EtOAc and washed with 1N HCl (aqueous), saturated NaHCO$_3$, and saturated brine. The organic phase was dried (Na$_2$SO$_4$), filtered and concentrated in vacuo to give 6.3 g of a pale brownish solid. Purification by flash chromatography using EtOAc/hexane (7/3) gave compound 15b as a white solid (3.94 g, 62%). HPLC (95%); MS (FAB) 242.1 (MH$^+$), 264.1 (MNa$^+$); $^1$H-NMR (DMSO-d$_6$) δ 8.10 (bs, 1H), 6.88 (d, J=7 Hz, 1H), 3.86 (m, 1H), 3.35–3.2 (m, 2H), 1.37 (s, 9H), 1.18 (d, J=7.3 Hz, 2H).

Synthesis of compound 15c:

To a solution of compound 15b (3.92 g, 17.5 mmol) in THF (350 mL) at 0° C. was added sequentially triphenylphosphine (7.2 g, 35.4 mmol), DEAD (5.5 mL, 35.1 mmol), and trimethylsilylazide (4.66 mL, 35.1 mmol). The reaction was warmed to RT and left to stir 16 h. The mixture was then heated to 70° C. for 4 h and stirred an additional 48 h at RT. The solution was cooled to 0° C. and treated with excess 5.5% aqueous (NH$_4$)$_2$Ce(NO$_3$)$_6$ [caution, add slowly dropwise]. The crude mixture was extracted with EtOAc (3×100 mL) and washed with saturated brine before being dried (Na$_2$SO$_4$), filtered and concentrated in vacuo. Purification by flash chromatography using EtOAc/hexane (6/4) gave compound 15c as a white solid (3.3 g, 76%). MS (FAB) 267.1 (MH); $^1$H-NMR (DMSO-d$_6$) δ 7.75 (d, J=, 1H), 5.1–5.02 (m, 1H), 4.73 (t, J=2H), 3.18 (t, J=2H), 1.49 (d, J=X, 3H), 1.36 (s, 9H).

Final deprotection of the tetrazole and the ester functionalities was accomplished by saponification. The protected peptide 15d (38 mg, 0.033 mmol) was dissolved in THF (0.5 mL), MeOH (0.25 mL) and H$_2$O (0.25 mL) before being treated with aqueous NaOH (0.1 mL of a 2 N solution, 0.198 mmol) for 4 h. The mixture was concentrated in vacuo and the crude product purified by preparative HPLC to give after lyophilization compound 233 as a white solid (7.5 mg, 25%). HPLC (98%); MS (FAB) 913.5 (M–H$^-$); HRMS calcd for C$_{41}$H$_{62}$N$_{12}$O$_{12}$ (MH$^+$) 915.4688, found: 915.47250. $^1$H-NMR (DMSO-d$_6$) δ 10.32 (bs, 1H), 8.23 (d, J=7.6 Hz, 1H), 8.05 (d, J=7.6 Hz, 1H), 7.99 (d, J=8.6 Hz, 1H), 7.90 (d, J=9.2 Hz, 1H), 7.35–7.27 (m, 5H), 6.99 (m, 1H), 5.12 (m, 1H), 4.56–4.42 (m, 4H), 4.41– 4.34 (m, 1H), 4.34–4.17 (m, 5H), 3.70 (dd, J=10.5, 10.5 Hz, 1H), 3.15 (bm, 1H), 2.67–2.61 (m, 2H), 2.48–2.40 (m, 1H), 2.30–2.23 (m, 1H), 2.22–2.15 (m, 2H), 2.02–1.92 (m, 2H), 1.87–1.81 (m, 1H), 1.80 (s, 3H), 1.77–1.67 (m, 1H), 1.67–1.57 (m, 1H), 1.51 (d, J=7 Hz, 3H), 1.45–1.27 (m, 3H), 1.06–0.94 (m, 1H), 0.87 (dd, J=6.4, 6.4 Hz, 6H), 0.82 (t, J=7.0 Hz, 3H), 0.72–0.62 (m, 6H).

Example 16

Synthesis of compound 107

To Boc-(L)Nvl-OH (0.28 g, 1.28 mmol) was added benzylamine (0.163 g, 1.53 mmol), TBTU (0.45 g, 1.41 mmol), and diisopropylethylamine (0.45 mL, 2.56 mmol) in DMF (10 mL) for 16 h. The reaction was concentrated and the residue dissolved in EtOAc (80 mL) and washed sequentially with saturated aqueous NaHCO$_3$, 10% aqueous HCl, and brine before being dried (MgSO$_4$), filtered and concentrated in vacuo to give a white solid (0.18 g, 46%) which was 91% homogeneous by analytical HPLC. This material (37 mg, 0.12 mmol) was treated with 4 N HCl, dioxane (5 mL) for 30 min before being concentrated in vacuo. The hydrochloride salt (0.12 mmol) was combined with the pentapeptide 10h (0.10 g, 0.11 mmol), TBTU (39 mg, 0.12 mmol) and diisopropylethylamine (0.07 mL, 0.38 mmol) in DMF (8 mL) and stirred for 16 h. The reaction mixture was concentrated and the residue dissolved in EtOAc and washed sequentially with saturated aqueous NaHCO$_3$, 10% aqueous HCl, and brine before being dried (MgSO$_4$), filtered, and concentrated in vacuo to give a white solid (0.12 g, 89%). The peptide was deprotected with neat TFA (5 mL) for 1 h before being concentrated. The compound was purified by preparative HPLC to give compound 107 (39 mg, 39%). HPLC (98.5%); FAB MS m/z: 908 (MH$^+$); HRMS calcd for C$_{46}$H$_{65}$N$_7$O$_{12}$ (MH$^+$) 908.47693, found: 908.47230; AAA OK; $^1$H-NMR (DMSO-d$_6$) • 12.5–11.9 (bs, 2H), 8.30 (t, J=5.7 Hz, 1H), 8.15 (d, J=7.3 Hz, 1H), 8.02 (m, 3H), 7.79 (d, J=6.8 Hz, 1H), 7.37–7.19 (m, 1OH), 4.57–4.39 (m, 3H), 4.33–4.14 (m, 6H), 4.11 (d, J=11.5 Hz, 1H), 3.68 (dd, J=10.8, 4.1 Hz, 1H), 2.63 (dd, J=16.2, 6.2 Hz, 1H), 2.45 (dd, J=16.2, 6.2 Hz, 1H), 2.23–2.15 (m, 3H), 2.02–1.85 (m, 3H), 1.82 (s, 3H), 1.79–1.67 (m, 2H), 1.66–1.48 (m, 2H), 1.40–1.23 (m, 3H), 1.08–0.97 (m, 1H), 0.92–0.81 (m, 11H), 0.73 (t, J=7.95 Hz, 6H).

Example 17

Synthesis of compound 108

Compound 108 was prepared according to the procedure for compound 107.

HPLC (99.9%); FAB MS m/z: 922 (MH$^+$); HRMS calcd for C$_{47}$H$_{67}$N$_7$O$_{12}$ (MH$^+$) 922.49261, found: 922.49560; $^1$H-NMR (DMSO-d$_6$) • 12.5–11.9 (bs, 2H), 8.21 (d, J=7.95 Hz, 1H), 8.15 (d, J=7.6 Hz, 1H), 8.05 (d, J=7.6 Hz, 2H), 7.91 (d, J=7.95 Hz, 1H), 7.79 (8.9 Hz, 1H), 7.36–7.25 (m, 1OH), 7.23–7.17 (m, 1H), 4.92–4.83 (m, 1H), 4.53 (m, 1H), 4.51 (d, J=7.95 Hz, 1H), 4.44 (d, J=7.95 Hz, 1H), 4.42 (m, 1H), 4.33–4.25 (m, 2H), 4.24–4.14 (m, 3H), 4.11 (d, J=11 Hz, 1H), 3.71 (m, 1H), 2.63 (dd, J=11.0, 4.0 Hz, 1H), 2.45 (dd, J=11.0, 4.0 Hz, 1H), 2.23–2.14 (m, 3H), 2.04–1.86 (m, 3H), 1.82 (s, 3H), 1.80–1.66 (m, 2H), 1.62–1.42 (m, 2H), 1.33 (d, J=7.0 Hz, 3H), 1.30–1.17 (m, 2H), 1.07–0.96 (m, 1H), 0.88 (m, 6H), 0.81 (t, J=7.3 Hz, 3H), 0.73 (t, J=7.6 Hz, 6H).

Example 18

Recombinant HCV NS3 Protease Radiometric Assay a) Cloning, expression and purification of the recombinant HCV NS3 protease type lb Serum from an HCV-infected patient was obtained through an external collaboration (Bernard Willems MD, Hôpital St-Luc, Montréal, Canada and Dr. Donald Murphy, Laboratoire de Santé Publique du Québec, Ste-Anne de Bellevue, Canada). An engineered full-length cDNA template of the HCV genome was constructed from DNA fragments obtained by reverse transcription-PCR (RT-PCR) of serum RNA and using specific primers selected on the basis of homology between other genotype lb strains. From the determination of the entire genomic sequence, a genotype 1b was assigned to the HCV isolate according to the classification of Simmonds et al. (J. Clin. Microbiol., (1993), 31, p.1493–1503). The amino acid sequence of the non-structural region, NS2-NS4B, was shown to be greater than 93% identical to HCV genotype 1b (BK, JK and 483 isolates) and 88% identical to HCV genotype 1a (HCV-1 isolate). A DNA fragment encoding the polyprotein precursor (NS3/NS4A/NS4B/NS5A/NS5B) was generated by PCR and introduced into eucaryotic expression vectors. After transient transfection, the polyprotein processing mediated by the HCV NS3 protease was demonstrated by the presence of the mature NS3 protein using Western blot analysis. The mature NS3 protein was not observed with expression of a polyprotein precursor containing the mutation S1165A, which inactivates the NS3 protease, confirming the functionality of the HCV NS3 protease.

The DNA fragment encoding the recombinant HCV NS3 protease (amino acid 1027 to 1206) was cloned in the pETlid bacterial expression vector. The NS3 protease expression in E. coli BL21(DE3)pLysS was induced by incubation with 1 mM IPTG for 3 h at 22° C. A typical fermentation (18 L) yielded approximately 100 g of wet cell paste. The cells were resuspended in lysis buffer (3.0 mL/g) consisting of 25 mM sodium phosphate, pH 7.5, 10% glycerol (v/v), 1 mM EDTA, 0.01% NP-40 and stored at −80° C. Cells were thawed and homogenized following the addition of 5 mM DTT. Magnesium chloride and DNase were then added to the homogenate at final concentrations of 20 mM and 20 μg/mL respectively. After a 25 min incubation at 4° C., the homogenate was sonicated and centrifuged at 15000× g for 30 min at 4° C. The pH of the supernatant was then adjusted to 6.5 using a 1M sodium phosphate solution.

An additional gel filtration chromatography step was added to the 2 step purification procedure described in WO 95/22985 (incorporated herein by reference). Briefly, the supernatant from the bacterial extract was loaded on a SP HiTrap column (Pharmacia) previously equilibrated at a flow rate of 2 mL/min in buffer A (50 mM sodium phosphate, pH 6.5, 10% glycerol, 1 mM EDTA, 5 mM DTT, 0.01% NP-40). The column was then washed with buffer A containing 0.15 M NaCl and the protease eluted by applying 10 column volumes of a linear 0.15 to 0.3 M NaCl gradient. NS3 protease-containing fractions were pooled and diluted to a final NaCl concentration of 0.1 M. The enzyme was further purified on a HiTrap Heparin column (Pharmacia) equilibrated in buffer B (25 mM sodium phosphate, pH 7.5, 10% glycerol, 5 mM DTT, 0.01% NP-40). The sample was loaded at a flow rate of 3 mL/min. The column was then washed with buffer B containing 0.15 M NaCl at a flow rate of 1.5 mL/min. Two step washes were performed in the presence of buffer B containing 0.3 or 1M NaCl. The protease was recovered in the 0.3M NaCL wash, diluted 3-fold with buffer B, reapplied on the HiTrap Heparin column and eluted with buffer B containing 0.4 M NaCl. Finally, the NS3 protease-containing fractions were applied on a Superdex 75 HiLoad 16/60 column (Pharmacia) equilibrated in buffer B containing 0.3 M NaCl. The purity of the HCV NS3 protease obtained from the pooled fractions was judged to be greater than 95% by SDS-PAGE followed by densitometry analysis.

The enzyme was stored at −80° C. and was thawed on ice and diluted just prior to use.

Example 19

Recombinant HCV NS3 Protease/NS4A Cofactor Peptide Radiometric Assay

The enzyme was cloned, expressed and prepared according to the protocol described in Example 18. The enzyme was stored at −80° C., thawed on ice and diluted just prior to use in the assay buffer containing the NS4A cofactor peptide.

The substrate used for the NS3 protease/N24A cofactor peptide radiometric assay, DDIVPC-SMSYTW, is cleaved between the cysteine and the serine residues by the enzyme. The sequence DDIVPC-SMSYTW corresponds to the NS5A/NS5B natural cleavage site in which the cysteine residue in P2 has been substituted for a proline. The peptide substrate DDIVPC-SMSYTW and the tracer biotin-DDIVPC-SMS [$^{125}$I-Y]TW are incubated with the recombinant NS3 protease and the NS4A peptide cofactor KKGS-VVIVGRIILSGRK (molar ratio enzyme: cofactor 1:100) in the absence or presence of inhibitors. The separation of substrate from products is performed by adding avidin-coated agarose beads to the assay mixture followed by filtration. The amount of SMS[$^{125}$I-Y]TW product found in the filtrate allows for the calculation of the percentage of substrate conversion and of the percentage of inhibition.

A. Reagents

Tris and Tris-HCl (UltraPure) were obtained from Gibco-BRL. Glycerol (UltraPure), MES and BSA were purchased from Sigma. TCEP was obtained from Pierce, DMSO from Aldrich and NaOH from Anachemia.

Assay buffer: 50 mM Tris HCl, pH 7.5, 30% (w/v) glycerol, 1 mg/mL BSA, 1 mM TCEP (TCEP added just prior to use from a 1 M stock solution in water)

Substrate: DDIVPCSMSYTW, 25 μL final concentration (from a 2 mM stock solution in DMSO stored at −20° C. to avoid oxidation).

Tracer: reduced mono iodinated substrate biotin DDIVPC SMS[$^{125}$I Y]TW (~1 nM final concentration). HCV NS3 protease type 1b, 25 nM final concentration (from a stock solution in 50 mM sodium phosphate, pH 7.5, 10% glycerol, 300 mM NaCl, 5 mM DTT, 0.01% NP-40).

NS4A Cofactor peptide: KKGSVVIVGRIILSGRK, 2.5 μM final concentration (from a 2 mM stock solution in DMSO stored at −20° C.).

B. Protocol

The assay was performed in a 96-well polypropylene plate from Costar. Each well contained:
20 μL substrate/tracer in assay buffer;
10 μL±inhibitor in 20% DMSO/assay buffer;
10 μL NS3 protease 1b/NS4 cofactor peptide (molar ratio 1:100).

Blank (no inhibitor and no enzyme) and control (no inhibitor) were also prepared on the same assay plate.

The enzymatic reaction was initiated by the addition of the enzyme/NS4A peptide solution and the assay mixture was incubated for 40 min at 23° C. under gentle agitation. Ten (10) μL of 0.5N NaOH were added and 10 μL 1 M MES, pH 5.8 were added to quench the enzymatic reaction.

Twenty (20) μL of avidin-coated agarose beads (purchased from Pierce) were added in a Millipore MADP N65 filtration plate. The quenched assay mixture was transferred to the filtration plate, and incubated for 60 min at 23° C. under gentle agitation.

The plates were filtered using a Millipore MultiScreen Vacuum Manifold Filtration apparatus, and 40 μL of the filtrate was transferred in an opaque 96-well plate containing 60 μL of scintillation fluid per well.

The filtrates were counted on a Packard TopCount instrument using a $^{125}$I-liquid protocol for 1 minute.

The %inhibition was calculated with the following equation:

$$100-[(\text{counts}_{inh}-\text{counts}_{blank})/(\text{counts}_{ctl}-\text{counts}_{blank})\times 100]$$

A non-linear curve fit with the Hill model was applied to the inhibition-concentration data, and the 50% effective concentration ($IC_{50}$) was calculated by the use of SAS software (Statistical Software System; SAS Institute, Inc., Cary, N.C.).

Example 20
Specificity Assays

The specificity of the compounds was determined against a variety of serine proteases: human leukocyte elastase, porcine pancreatic elastase and bovine pancreatic α-chymotrypsin and one cysteine protease: human liver cathepsin B. In all cases a 96-well plate format protocol using a calorimetric p-nitroanilide (pNA) substrate specific for each enzyme was used. Each assay included a 1 h enzyme-inhibitor pre-incubation at 30° C. followed by addition of substrate and hydrolysis to ≈30% conversion as measured on a UV Thermomax® microplate reader. Substrate concentrations were kept as low as possible compared to $K_M$ to reduce substrate competition. Compound concentrations varied from 300 to 0.06 μM depending on their potency. The final conditions for each assay were as follows: 50 mM Tris-HCl pH 8, 0.5 M $Na_2SO_4$, 50 mM NaCl, 0.1 mM EDTA, 3% DMSO, 0.01% Tween-20 with;
[100 μM Succ-AAPF-pNA and 250 pM α-chymotrypsin], [133 μM Succ-AAA-pNA and 8 nM porcine elastase], [133 μM Succ-AAV-pNA and 8 nM Leukocyte elastase]; or [100 mM $NaHPO_4$ pH 6, 0.1 mM EDTA, 3% DMSO, 1 mM TCEP, 0.01% Tween-20, 30 μM Z-FR-pNA and 5 nM cathepsin B (the stock enzyme was activated in buffer containing 20 mM TCEP before use)].

A representative example is summarized below for porcine pancreatic elastase:

In a polystyrene flat-bottom 96-well plate were added using a Biomek liquid handler (Beckman):
40 μL of assay buffer (50 mM Tris-HCl pH 8, 50 mM NaCl, 0.1 mM EDTA);
20 μL of enzyme solution (50 mM Tris-HCl pH 8, 50 mM NaCl, 0.1 mM EDTA, 0.02% Tween-20, 40 nM porcine pancreatic elastase); and
20 μL of inhibitor solution (50 mM Tris-HCl, pH 8, 50 mM NaCl, 0.1 mM EDTA, 0.02% Tween-20, 1.5 mM–0.3 μM inhibitor, 15% v/v DMSO).

After 60 min pre-incubation at 30° C., 20 μL of substrate solution (50 mM Tris-HCl, pH 8, 0.5 m $Na_2SO_4$, 50 mM NaCl, 0.1 mM EDTA, 665 μM Succ-AAA-pNA) were added to each well and the reaction was further incubated at 30° C. for 60 min after which time the absorbance was read on the UV Thermomax® plate reader. Rows of wells were allocated for controls (no inhibitor) and for blanks (no inhibitor and no enzyme).

The sequential 2-fold dilutions of the inhibitor solution were performed on a separate plate by the liquid handler using 50 mM Tris-HCl pH 8, 50 mM NaCl, 0.1 mM EDTA, 0.02% Tween-20, 15% DMSO. All other specificity assays were performed in a similar fashion.

The percentage of inhibition was calculated using the formula:

$$[1-(UV_{inh}-UV_{blank})/(UV_{ctl}-UV_{blank}))]\times 100$$

A non-linear curve fit with the Hill model was applied to the inhibition-concentration data, and the 50% effective concentration ($IC_{50}$) was calculated by the use of SAS software (Statistical Software System;

SAS Institute, Inc., Cary, N.C.).

Example 21
Tables of compounds

The following tables list $IC_{50}$ values of compounds representative of the invention.

The following abbreviations are used:

$IC_{50}$: The concentration required to obtain 50% inhibition in the NS3 protease/NS4A cofactor peptide radiometric assay according to Example 19.

HLE: The concentration required to obtain 50% inhibition in the human leukocyte elastase assay;

PPE: The concentration required to obtain 50% inhibition in the porcine pancreatic elastase assay;

Other: Figures unmarked indicate the concentration required to obtain 50% inhibition in the bovine pancreatic α-chymotrypsin assay; figures marked with ** indicate the concentration required to obtain 50% inhibition in the human liver cathepsin B assay; MS: Mass spectrometric data ($MH^+$ from FAB); AAA: amino acid analysis data expressed in % peptide recovery;

Acpr: 1-amino-cyclopropylcarboxylic acid; Acpe: 1-amino-cyclopentylcarboxylic acid; Abu: aminobutyric acid; Chg: cyclohexylglycine (2-amino-2-cyclohexyl-acetic acid); Hyp: 4(R)-hydroxyproline; Hyp(4-Bn): 4(R)-benzyloxyproline; Pip: pipecolic acid; Tbg: tert-butylglycine; Ac: acetyl; Bn: benzyl; O—Bn: benzyloxy; DAD: 3-carboxypropionyl; and DAE: 4-carboxybutyryl.

TABLE 1

| cpd | B | P6 | P5 | P4 | P3 | $R_2$ | $R_1$ | $R_{13}$ | $IC_{50}$ ($\mu M$) | HLE ($\mu M$) | PPE ($\mu M$) | OTHER ($\mu M$) | MS ($MH^+$) | AAA (%) |
|---|---|---|---|---|---|---|---|---|---|---|---|---|---|---|
| 101 | Ac | Asp | D-Glu | Ile | Val | O—Bn | ethyl | $CF_3$ | 9.4 | <1.2 | | | 857.4 | |
| 102 | Ac | Asp | D-Glu | Ile | Val | O—Bn | propyl | $CF_2CF_3$ | 0.21 | | | | 921 | 99.2 |
| 103 | Ac | Asp | D-Glu | Ile | Val | O—Bn | propyl | C(O)NH—Bn | 0.023 | | | | 936 | |
| 104 | Ac | Asp | D-Glu | Ile | Val | O—Bn | propyl | H | 0.14 | 7 | 8 | 8 | 803 | 115 |
| 105 | Ac | Asp | D-Glu | Ile | Val | O—Bn | propyl | $NH_2$ | 54 | | | | 818 | 108 |
| 106 | Ac | Asp | D-Glu | Ile | Val | O—Bn | propyl | $CH_2CH_2$—Ph | 5.4 | 16 | | | 908 | 107.8 |
| 107 | Ac | Asp | D-Glu | Ile | Val | O—Bn | propyl | $NHCH_2Ph$ | 3 | | | | 908 | 100.8 |
| 108 | Ac | Asp | D-Glu | Ile | Val | O—Bn | propyl | (S)—NH—CH(Me)Ph | 0.71 | 3 | >300 | >300 | 922 | 107 |
| 109 | Ac | — | — | Chg | Val | O—Bn | propyl | C(O)—NHBn | 23 | 2 | | | 718.3 | |
| 110 | Ac | Asp | D-Glu | Ile | Val | O—Bn | propyl | (tetrahydroisoquinoline-3-carboxylic acid) | 8 | | | | ($MH^-$) 753.5 | |
| 111 | Ac | Asp | D-Glu | Ile | Val | O—Bn | propyl | (tetrahydroisoquinoline) | 20 | | | | | |
| 112 | Ac | Asp | D-Glu | Ile | Val | H | propyl | C(O)—NH—Bn | 2 | 0.03 | <0.06 | 10.3 | 814.4 | 104.4 |
| 113 | Ac | Asp | D-Glu | Ile | Val | H | propyl | $CF_2$—$CF_3$ | 12.8 | 0.07 | <0.06 | 18 | | |
| 114 | Ac | Asp | D-Glu | Ile | Val | H | propyl | $CF_3$ | 23.5 | 0.05 | 0.2 | 4.4 | 749.3 | 106.7 |
| 115 | Ac | Asp | D-Glu | Ile | Val | H | propyl | C(O)NHBn | 0.66 | 0.11 | <0.06 | 30 | 814 | 99.4 |
| 116 | Ac | — | — | Chg | Val | O—Bn | propyl | C(O)NH—$CH_2$-4-pyridine | 25 | | | | | |

TABLE 2

| entry # | B | P6 | P5 | P4 | P3 | R2 | R1 | X | R13 | IC50 (μM) | HLE (μM) | PPE (μM) | MS (MH+) | AAA (%) |
|---|---|---|---|---|---|---|---|---|---|---|---|---|---|---|
| 201 | Ac | Asp | D-Glu | Ile | Val | O—Bn | Propyl | O | NHCH2—C(O)OEt | 3.9 | 27.4 | 168 | 905.2 | |
| 202 | Ac | Asp | D-Glu | Ile | Val | O—Bn | Propyl | O | CH2CH2—Ph | 0.63 | 5.5 | | 908.4 | |
| 203 | Ac | Asp | D-Glu | Ile | Val | O—Bn | Propyl | O | NHCH2—Ph | 0.59 | | | 909.6 | |
| 204 | Ac | Asp | D-Glu | Ile | Val | O—Bn | Propyl | O | (R)—NH—CH(Me)Ph | 4.2 | | | 923.6 | |
| 205 | Ac | Asp | D-Glu | Ile | Val | O—Bn | Propyl | O | (S)—NH—CH(Me)Ph | 0.078 | 5.1 | 4.1 | 923.6 | 93.4 |
| 206 | Ac | Asp | D-Glu | Ile | Val | O—Bn | Propyl | O | OCH2Ph | 0.79 | <0.6 | <0.6 | 910 | 95.6 |
| 207 | Ac | Asp | D-Glu | Ile | Val | O—Bn | Propyl | O | NHCH2—C(O)OH | 3.75 | | | 877.1 | 106.5 |
| 208 | Ac | Asp | D-Glu | Ile | Val | O—Bn | Propyl | O | CH3 | 14.5 | | | 818.2 | 101.9 |
| 209 | Ac | Asp | D-Glu | Ile | Val | O—Bn | Propyl | O | NH2 | 20.5 | | | 819.3 | 100.6 |
| 210 | Ac | Asp | D-Glu | Ile | Val | O—Bn | Butyl | O | (S)—NH—CH(Me)Ph | 0.085 | 4 | | 937.5 | 95.4 |
| 211 | Ac | Asp | D-Glu | Ile | Val | O—Bn | Butyl | O | NH2 | 47 | | | 833 | 84 |
| 212 | Ac | Asp | D-Glu | Ile | Val | O—Bn | Propyl | O | (S)—NH—CH(Me)-naphtyl | 0.58 | 0.4 | | 974.3 | 98.9 |
| 213 | Ac | Asp | D-Glu | Ile | Val | O—Bn | Ethyl | O | (S)—NH—CH(Me)Ph | 0.079 | 36 | | 909.9 | 103.3 |
| 214 | Ac | Asp | D-Glu | Ile | Val | O—Bn | Propyl | O | (S)—NH—CH(Et)Ph | 0.44 | | | 937.5 | |
| 215 | Ac | — | D-Glu | Chg | Val | O—Bn | Propyl | O | (S)—NH—CH(Me)Ph | 45 | 5 | | 705.5 (MH−) | 95.8 |
| 216 | Ac | Asp | D-Glu | Ile | Val | O—Bn | propyl | O | (R)—NH—CH(OH)Ph | 9.6 | | | 908.5 | |
| 217 | Ac | Asp | D-Glu | Ile | Val | H | propyl | O | (S)—NH—CH(Me)Ph | 1.04 | | | 803.4 | 93.2 |
| 218 | Ac | Asp | D-Glu | Ile | Val | O—Bn | isopentyl | O | (S)—NH—CH(Me)Ph | 3.3 | | | 951.5 | 99.5 |
| 219 | Ac | Asp | D-Glu | Ile | Val | O—Bn | pentyl | O | (S)—NH—CH(Me)Ph | 0.43 | 151 | | 951.5 | |
| 220 | HOOC(CH2)2—C(O) | — | D-Asp | Ile | Val | H | propyl | O | (S)—NH—CH(Me)Ph | 6.9 | | | (MH−) 744.5 | 97.5 |
| 221 | Ac | Asp | D-Glu | Ile | Val | O—Bn | Me | O | (S)—NH—CH(Me)Ph | 0.52 | 168 | | 895 | 94 |
| 222 | Ac | Asp | D-Glu | Ile | Val | O—Bn | (CH2)2—isopropyl | O | (S)—NH—CH(Me)Ph | 8.9 | >300 | | 951.4 | 98.2 |
| 223 | Ac | Asp | D-Glu | Ile | Val | O—Bn | propyl | O | N(CH3)—Bn | 11 | | | 923.5 | 105.5 |

TABLE 2-continued
| entry # | B | P6 | P5 | P4 | P3 | R2 | R1 | X | R13 | IC50 (μM) | HLE (μM) | PPE (μM) | MS (MH+) | AAA (%) |
|---|---|---|---|---|---|---|---|---|---|---|---|---|---|---|
| 224 | Ac | Asp | D-Glu | Ile | Val | O—Bn | propyl | S | NH—Bn | 5 | | | (MH−) 923.4 | |
| 225 | Ac | Asp | D-Glu | Ile | Val | O—Bn | propyl | O | COCH3 | 13 | | | 862.3 | 102.3 |
| 226 | Ac | Asp | D-Glu | Ile | Val | O—Bn | propyl | O | 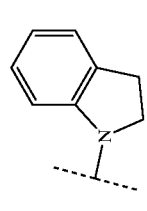 | 6.3 | | | 921.3 | 112.8 |
| 227 | Ac | — | — | Chg | Val | O—Bn | propyl | O | COOH | 39.5 | | | (MH−) 628.3 | |
| 228 | Ac | Asp | D-Glu | Ile | Val | O—Bn | CH2—CF3 | O | (S)—NH—CH(Me)Ph | 0.63 | | | (MH−) 961.4 | |
| 229 | Ac | Asp | D-Glu | Ile | Val | O—Bn | propyl | O | 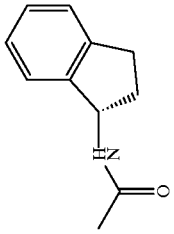 | 0.13 | 3.1 | | (MH−) 933.4 | 94.1 |
| 230 | Ac | Asp | D-Glu | Ile | Val | O—Bn | propyl | O | (S)—NH—CH(Me) | 0.36 | | | 929.5 | 100.6 |
| 231 | Ac | Asp | D-Glu | Ile | Val | O—Bn | propyl | O | 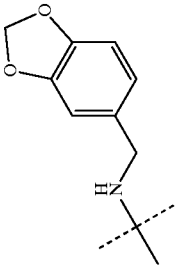 | 0.5 | | | 953.4 | 107.3 |

TABLE 2-continued
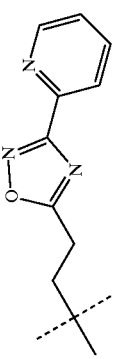
| entry # | B | P6 | P5 | P4 | P3 | R2 | R1 | X | R13 | IC$_{50}$ (μM) | HLE (μM) | PPE (μM) | MS (MH$^+$) | AAA (%) |
|---|---|---|---|---|---|---|---|---|---|---|---|---|---|---|
| 232 | Ac | Asp | D-Glu | Ile | Val | O—Bn | propyl | O | 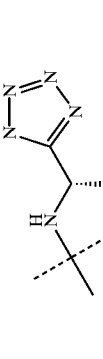 | 3.2 | | | 977.4 | 96.9 |
| 233 | Ac | Asp | D-Glu | Ile | Val | O—Bn | propyl | O |  | 1.5 | | | (MH$^-$) 913.5 | |
| 234 | Ac | Asp | D-Glu | Ile | Val | O—Bn | CH$_2$—CH=CH$_2$ | O | N-benzyl | 3.7 | | | 907.5 | |

TABLE 3

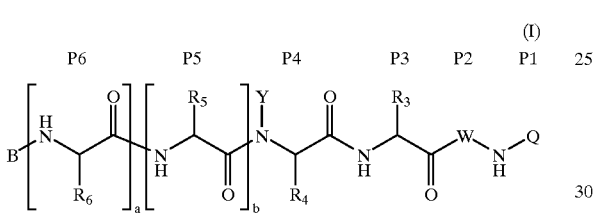

| entry # | B | P6 | P5 | P4 | P3 | R$_2$ | R$_1$ | R$_{15}$ | R$_{16}$ | IC$_{50}$ (μM) | HLE (μM) | PPE (μM) | OTHER (μM) | MS (MH$^+$) | AAA (%) |
|---|---|---|---|---|---|---|---|---|---|---|---|---|---|---|---|
| 301 | Ac | Asp | D-Glu | Ile | Val | O—Bn | propyl | O—Ph | O—Ph | 0.029 | <0.6 | <0.6 | 3 >300 | 1007 | 86.6 |
| 302 | Ac | Asp | D-Glu | Ile | Val | O—Bn | propyl | O—Ph | O—Ph | 26 | | | | 1007 | |

What is claimed is:

1. A compound of formula I:

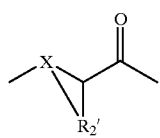

(I)

wherein B is an acyl derivative of formula R$_{11}$—C(O)— wherein R$_{11}$ is C$_{1-10}$ alkyl optionally substituted with carboxyl; or R$_{11}$ is C$_6$ or C$_{10}$ aryl or C$_{7-16}$ aralkyl optionally substituted with a C$_{1-6}$ alkyl;

a is 0 or 1;

R$_6$, when present, is the side chain of Asp or Glu, b is 0 or 1;

R$_5$, when present, is the side chain of D-Asp, D-Val, or D-Glu;

Y is H or C$_{1-6}$ alkyl;

R$_4$ is C$_{1-10}$ alkyl or C$_{3-10}$ cycloalkyl;

R$_3$ is C$_{1-10}$ alkyl or C$_{3-10}$ cycloalkyl;

W is a group of formula II':

Formula II'

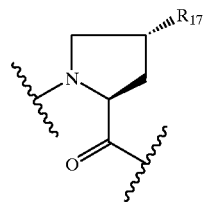

wherein X' is N; and

R$_2$' is the side chain of proline and is substituted with R$_{17}$ at the 4-position with the stereochemistry shown in formula III':

Formula III'

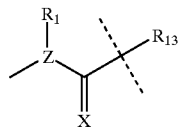

wherein R$_{17}$ is C$_6$ or C$_{10}$ aryl, C$_{7-16}$ aralkyl, S—C$_6$ or C$_{10}$ aryl or S—C$_{7-16}$ aralkyl, each optionally substituted with C$_{1-6}$ alkyl, NH$_2$, OH, SH, halo, carboxyl or carboxy(lower)alkyl, said aryl or aralkyl optionally containing at least one heteroatom selected independently from the group consisting of: O, S, and N; and said aryl and aralkyl optionally fused with a second 5-, 6- or 7-membered ring to form cyclic system or heterocycle, said second ring being optionally substituted with NH$_2$, OH, SH, halo, carboxy or carboxy (lower)alkyl, and said second ring optionally containing at least one heteroatom selected independently from the group consisting of: O, S, and N;

or R$_{17}$ is OR$_{12}$ wherein R$_{12}$ is a C$_6$ or C$_{10}$ aryl or C$_{7-16}$ aralkyl said first aryl or aralkyl optionally substituted with C$_{1-6}$ alkyl, C$_{3-7}$ cycloalkyl, NH$_2$, OH, SH, halo, C$_{1-6}$ alkoxy, carboxyl, carboxy(lower)alkyl, or a second aryl or aralkyl; said first and second aryl or aralkyl optionally containing at least one heteroatom selected independently from the group consisting of: O, S, and N;

Q is a group of the formula:

wherein Z is CH or N;

X is O or S;

R$_1$ is H, C$_{1-6}$ alkyl or C$_{1-6}$ alkenyl both optionally substituted with thio or halo; and when Z is CH, then R$_{13}$ is H; CF$_3$; CF$_2$CF$_3$; CH$_2$—R$_{14}$; CH(F)—R$_{14}$; CF$_2$—R$_{14}$; NR$_{14}$R$_{14}$'; S—R$_{14}$; or CO—NH—R$_{14}$, wherein $R_{14}$ and $R_{14}'$ are independently hydrogen, cyclic $C_{3-10}$ alkyl or acyclic $C_{1-10}$ alkyl or cyclic $C_{3-10}$ alkenyl or acyclic $C_{2-10}$ alkenyl, said alkyl or alkenyl optionally substituted with $NH_2$, OH, SH, halo or carboxyl; said alkyl or alkenyl optionally containing at least one heteroatom selected independently from the group consisting of: O, S, and N; or $R_{14}$ and $R_{14}'$ are independently $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl or substituted with a further $C_{3-7}$ cycloalkyl, $C_6$ or $C_{10}$ aryl, or heterocycle; said aryl or aralkyl optionally containing at least one heteroatom selected independently from the group consisting of: O, S, and N.;

said cyclic alkyl, cyclic alkenyl, aryl or aralkyl being optionally fused with a second 5-, 6-, or 7-membered ring to form a cyclic system or heterocycle, said second ring being optionally substituted with $NH_2$, OH, SH, halo, carboxyl or carboxy(lower)alkyl or substituted with a further $C_{3-7}$ cycloalkyl, $C_6$ or $C_{10}$ aryl, or heterocycle; said second ring optionally containing at least one heteroatom selected independently from the group consisting of: O, S, and N;

or $R_{14}$ and $R_{14}'$ are independently $C_{1-4}$ alkyl which when joined together with N form a 3 to 6-membered nitrogen-containing ring which is optionally fused with a further $C_{3-7}$ cycloalkyl, $C_6$ or $C_{10}$ aryl or heterocycle;

with the proviso that when Z is CH, $R_{13}$ is $N(R_{14})R_{14}'$, $R_{14}$ is H and $R_{14}'$ is cyclic $C_{3-10}$ alkyl or acyclic $C_{1-10}$ alkyl or cyclic $C_{3-10}$ alkenyl or acyclic $C_{2-10}$ alkenyl, each substituted with carboxyl, then said carboxyl is not on the α-carbon of said alkyl or alkenyl and $R_{13}$ is not an α-amino acid;

when Z is N, then $R_{13}$ is H; carboxy; $C_{1-6}$ alkyl optionally substituted with carboxy; $CH_2$—$R_{14}$; $CHR_{14}R_{14}'$; $CH(F)$—$R_{14}$; O—$R_{14}$; $NR_{14}R_{14}'$ or S—$R_{14}$, wherein $R_{14}$ and $R_{14}'$ are as defined above; or Q is a phosphonate group of the formula:

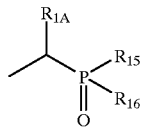

wherein $R_{15}$ and $R_{16}$ are independently $C_{6-20}$ aryloxy; and $R_{1A}$ is the same as $R_1$ as defined above.

2. A compound of formula I according to claim 1, wherein Q is a group of the formula:

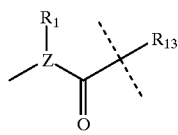

wherein Z is CH or N;

$R_1$ is hydrogen, $C_{1-6}$ alkyl optionally substituted with thiol, or $C_{1-6}$ alkenyl; and when Z is CH, then $R_{13}$ is H; $CF_3$; $CF_2CF_3$; $CH_2$—$R_{14}$; $CH(F)$—$R_{14}$; $CF_2$—$R_{14}$; $NR_{14}R_{14}'$ S—$R_{14}$; $CHR_{14}R_{14}'$ or CO—NH—$R_{14}$ wherein $R_{14}$ and $R_{14}'$ are independently hydrogen, cyclic $C_{3-10}$ alkyl or acyclic $C_{1-10}$ alkyl or cyclic $C_{3-10}$ alkenyl or acyclic $C_{2-10}$ alkenyl, said alkyl or alkenyl optionally substituted with $NH_2$, OH, SH, halo or carboxyl; said alkyl or alkenyl optionally containing at least one heteroatom selected independently from the group consisting of: O, S, and N; or $R_{14}$ and $R_{14}'$ are independently $C_6$ or $C_{10}$ aryl or $C_{7-16}$ aralkyl optionally substituted with $C_{1-6}$ alkyl, $NH_2$, OH, SH, halo, carboxyl or carboxy(lower)alkyl; said aryl or aralkyl optionally containing at least one heteroatom selected independently from the group consisting of: O, S, and N;

said cyclic alkyl, cyclic alkenyl, aryl or aralkyl being optionally fused with a second 5-, 6-, or 7-membered ring to form a cyclic system or heterocycle, said second ring being optionally substituted with $NH_2$, OH, SH, halo, carboxyl or carboxy(lower)alkyl; said second ring optionally containing at least one heteroatom selected independently from the group consisting of: O, S, and N;

with the proviso that, when Z is CH, then $R_{13}$ is not an α-amino acid;

when Z is N, then $R_{13}$ is H; $CH_3$; $NH_2$; $CH_2$—$R_{14}$; CH (F)—$R_{14}$; $CHR_{14}R_{14}'$; O—$R_{14}$; NH—$R_{14}$; $NR_{14}R_{14}'$ or S—$R_{14}$ wherein $R_{14}$ and $R_{14}'$ are as defined above.

3. The compound of formula I according to claim 1, wherein B is an acyl derivative of formula $R_{11}C(O)$— wherein $R_{11}$ is:

$C_{1-6}$ alkyl optionally substituted with carboxyl, $C_{1-6}$ alkanoyloxy or $C_{1-6}$ alkoxy;

$C_{3-7}$ cycloalkyl optionally substituted with carboxyl, MeOC(O), EtOC(O) or BnOC(O);

3-carboxypropionyl or 4-carboxybutyryl; or

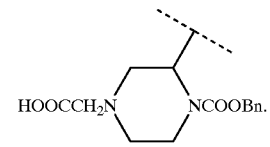

4. The compound of formula I according to claim 3, wherein B is acetyl, 3-carboxypropionyl, 4-carboxylbutyryl, $AcOCH_2C(O)$, $Me_3COC(O)$,

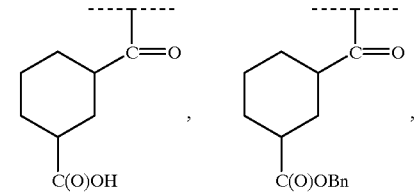

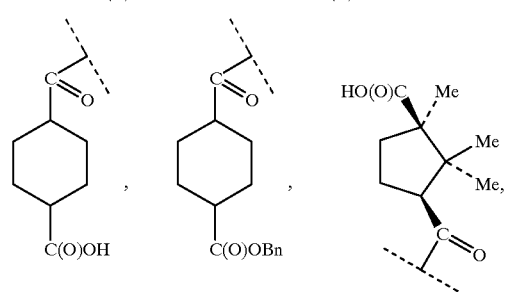

-continued

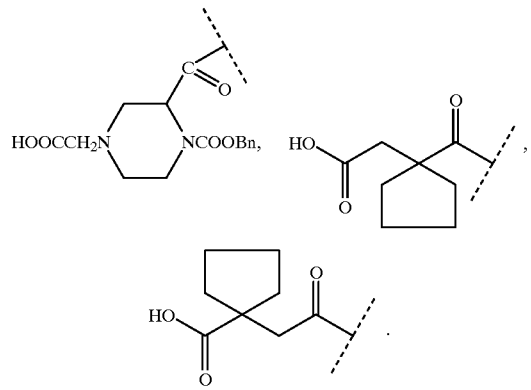

5. The compound of formula I according to claim 4, wherein B is acetyl, 3-carboxypropionyl, 4-carboxybutyryl, AcOCH$_2$C(O),

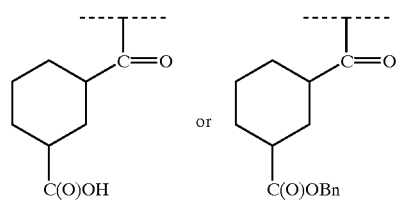

6. The compound of formula I according to claim 5, wherein B is acetyl, or 4-carboxybutyryl.

7. The compound of formula I according to claim 6, wherein B is acetyl.

8. The compound of formula I according to claim 1, wherein R$_6$, when present, is the side chain of Asp.

9. The compound of formula I according to claim 1, wherein a is 0 and then R$_6$ is absent.

10. The compound of formula I according to claim 1, wherein R$_5$, when present, is the side chain of D-Glu.

11. The compound of formula I according to claim 1, wherein a is 0 and b is 0, and then both R$_6$ and R$_5$ are absent.

12. The compound of formula I according to claim 1, wherein R$_4$ is the side chain of an amino acid selected from the group consisting of: Val, cyclohexylglycine (Chg), Tbg, Ile, and Leu.

13. The compound of formula I according to claim 12, wherein R$_4$ is the side chain of Chg or Ile.

14. The compound of formula I according to claim 13, wherein R$_4$ is the side chain of Chg.

15. The compound of formula I according to claim 1, wherein R$_3$ is the side chain of an amino acid selected from the group consisting of: Ile, Chg, Cha, Val and Glu.

16. The compound of formula I according to claim 15, wherein R$_3$ is the side chain of Val or Chg.

17. The compound of formula I according to claim 16, wherein R$_3$ is the side chain of Val.

18. The compound of formula I according to claim 1, wherein R$_{17}$ is Bn, PhCH$_2$CH$_2$, PhCH$_2$CH$_2$CH$_2$, O—Bn, o-tolylmethoxy, m-tolylmethoxy, p-tolylmethoxy, 1-naphthalenylmethoxy, 2-naphthalenylmethoxy, (4-tert-butyl)methoxy, (3I—Ph)CH$_2$O, (4Br—Ph)O, (2Br—Ph)O, (3Br—Ph)O, (4I—Ph)O, (3Br—Ph)CH$_2$O, (3,5—Br$_2$—Ph)CH$_2$O,

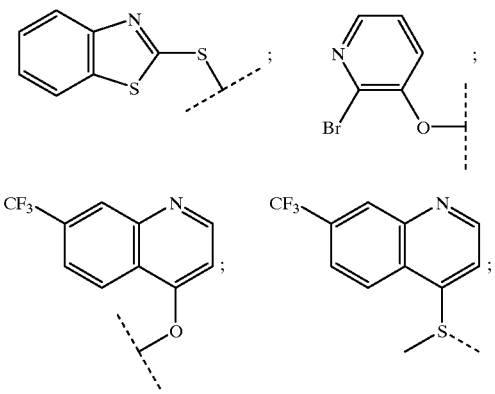

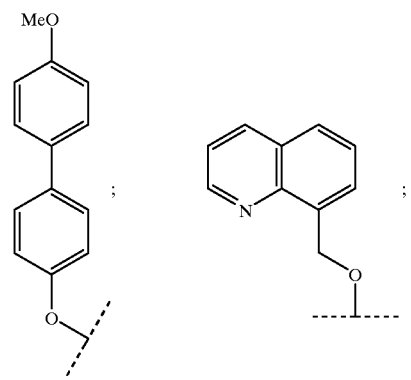

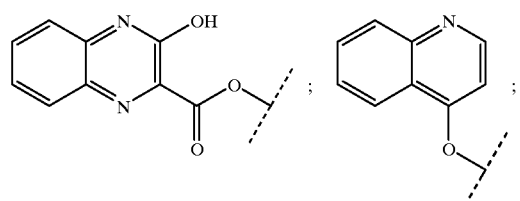

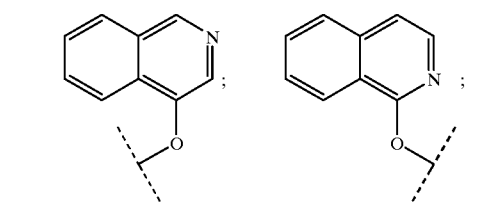

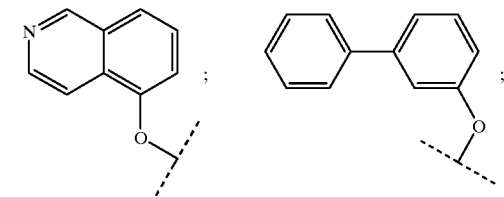

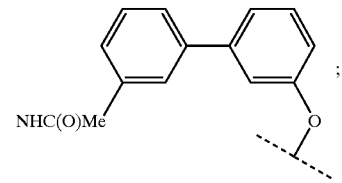

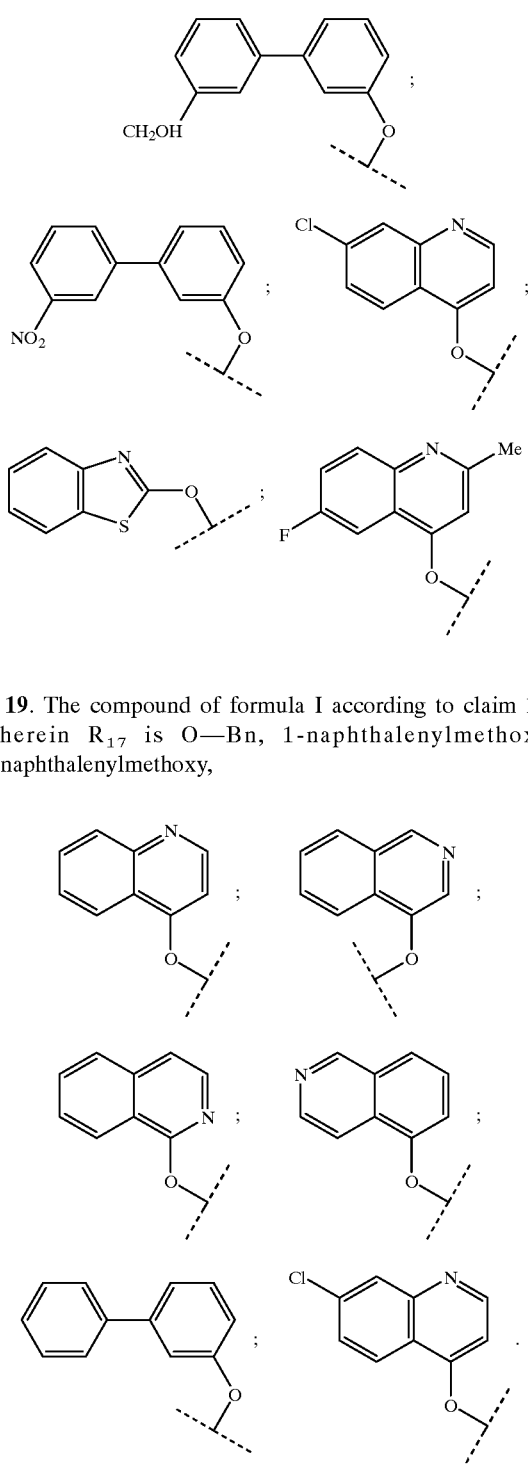

19. The compound of formula I according to claim 18, wherein $R_{17}$ is O—Bn, 1-naphthalenylmethoxy, 2-naphthalenylmethoxy,

20. The compound of formula I according to claim 18, wherein $R_{17}$ is O—Bn, 1-naphthalenylmethoxy, or 2-naphthalenylmethoxy.

21. The compound of formula I according to claim 1, wherein Q is:

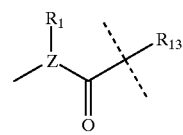

wherein Z is CH or N;

when Z is CH: $R_{13}$ is H; $CF_3$; $CF_2CF_3$; $CH_2$—$R_{14}$; C(O)NH—$R_{14}$, $NR_{14}R_{14'}$ wherein $R_{14}$ and $R_{14'}$ are as defined in claim 1 with the proviso that $R_{13}$ is not an α-amino acid; and when Z is N: $R_{13}$ is phenyl, or $C_{7-16}$ aralkyl,

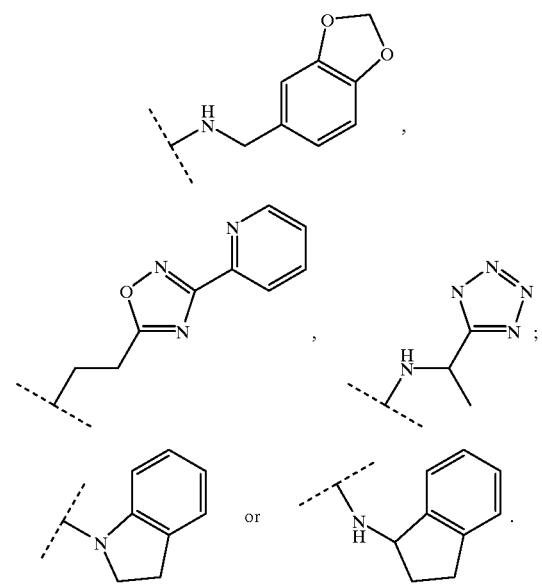

22. The compound of formula I according to claim 21, wherein when Z is CH: $R_{13}$ is H; NH—$R_{14}$ or C(O)NH—$R_{14}$; wherein $R_{14}$ is phenyl or $C_{7-16}$ aralkyl.

23. The compound of formula I according to claim 22, wherein $R_{13}$ is H; or C(O)NH—$R_{14}$; and $R_{14}$ is benzyl or CH(Me)Ph.

24. The compound of formula I according to claim 21, wherein when Z is N: $R_{13}$ is naphthyl, NH—CH(Me)Ph, NH—CH(Et)Ph, 25. The compound of formula I according to claim 24, wherein $R_{13}$ is NH—CH(Me)Ph, or

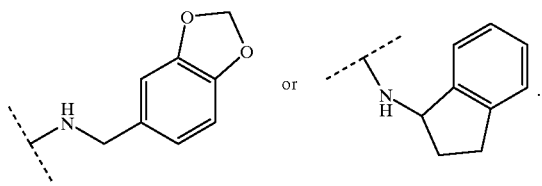

26. The compound of formula I according to claim 1, wherein Q is a phosphonate group of the formula:

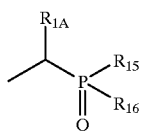

wherein $R_{15}$ and $R_{16}$ are independently $C_{6-12}$ aryloxy, and $R_{1A}$ is as defined in claim 1.

27. The compound of formula I according to claim 26, wherein $R_{15}$ and $R_{16}$ are each phenoxy.

28. The compound of formula I according to claim 1, wherein $R_1$ and $R_{1A}$ are independently $C_{1-6}$ alkyl or $C_{1-6}$ alkenyl optionally substituted with halo.

29. The compound of formula I according to claim 28, wherein $R_1$ and $R_{1A}$ are independently $C_{1-5}$ alkyl or $C_{1-4}$ alkenyl optionally substituted with fluoro.

30. The compound of formula I according to claim 29, wherein $R_1$ and $R_{1A}$ are independently ethyl, propyl, isopentyl, or allyl.

31. The compound of formula I according to claim 1, wherein B is an acyl derivative of formula $R_{11}C(O)$— wherein $R_{11}$ is: $C_{1-6}$ alkyl optionally substituted with carboxyl, $C_{1-6}$ alkanoyloxy or $C_{1-6}$ alkoxy; $C_{3-7}$ cycloalkyl optionally substituted with carboxyl, MeOC(O), EtOC(O) or BnOC(O); 3-carboxypropionyl or 4-carboxybutyryl; or

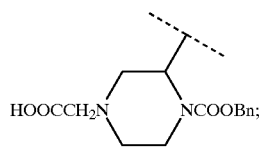

Y is H or $C_{1-3}$ alkyl;

$R_4$ is the side chain of an amino acid selected from the group consisting of: Val, cyclohexylglycine (Chg), Tbg, Ile, and Leu;

$R_3$ is the side chain of an amino acid selected from the group consisting of: Ile, Chg, Cha, Val and Glu;

W is:

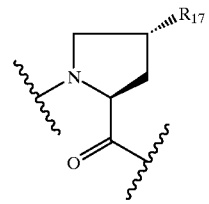

wherein $R_{17}$ is $OR_{12}$ wherein $R_{12}$ is a $C_6$ or $C_{10}$ aryl or $C_{7-16}$ aralkyl, said first aryl or aralkyl optionally substituted with $C_{1-6}$ alkyl, $C_{3-7}$ cycloalkyl, $NH_2$, OH, SH, halo, $C_{1-6}$ alkoxy, carboxyl, carboxy(lower)alkyl, or a second aryl or aralkyl; said first and second aryl or aralkyl optionally containing at least one heteroatom selected independently from the group consisting of: O, S, and N;

Q is:

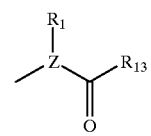

wherein Z is N; and $R_{13}$ is phenyl, $C_{7-16}$ aralkyl,

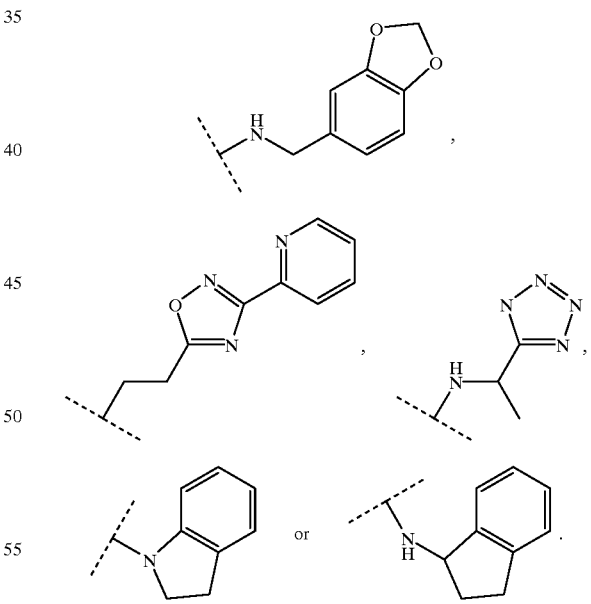

and $R_1$ and $R_{1A}$ are independently $C_{1-6}$ alkyl or $C_{1-6}$ alkenyl optionally substituted with halo.

32. The compound of formula I according to claim 31, wherein B is acetyl, 3-carboxypropionyl, 4-carboxybutyryl, $AcOCH_2C$ (O),

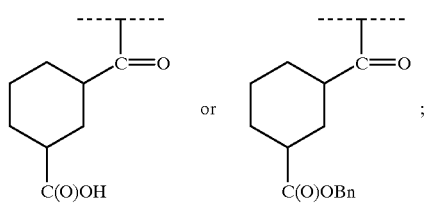

R$_6$, when present, is the side chain of Asp, or R$_6$ is absent;
R$_5$, when present, is the side chain of D-Glu;
or R$_5$ is absent;
R$_4$ is the side chain of Chg;
R$_3$ is the side chain of Val;
W is

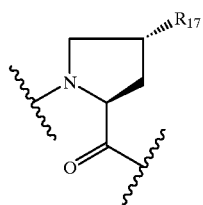

wherein R$_{17}$ is Bn; PhCH$_2$CH$_2$; PhCH$_2$CH$_2$CH$_2$; O—Bn; 1-naphtyloxy; 2-naphtyloxy; 1-naphthalenylmethoxy; 2-naphthalenylmethoxy;

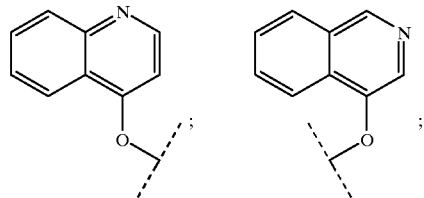

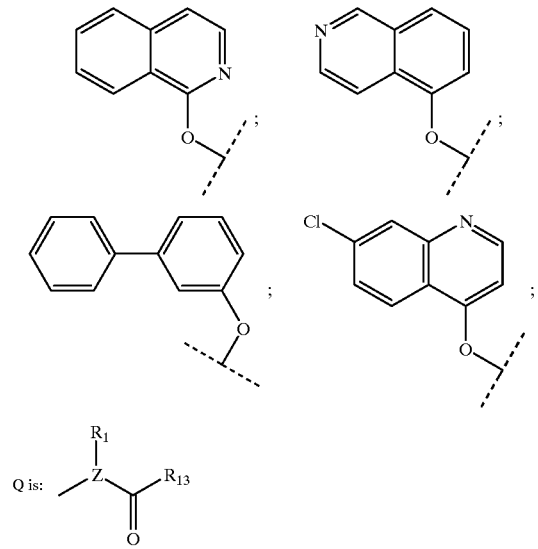

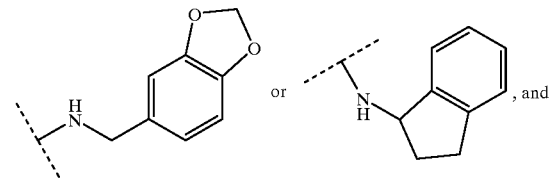

wherein R$_{13}$ is, NH—CH(Me)Ph, or

R$_1$ and R$_{1A}$ are independently ethyl, propyl, isopentyl, or allyl.

33. A method for treating or preventing the contamination of a material by the hepatitis C virus comprising contacting said material with an effective amount of a compound of formula I according to claim 1.

* * * * *

UNITED STATES PATENT AND TRADEMARK OFFICE
CERTIFICATE OF CORRECTION

PATENT NO.  : 6,143,715
DATED       : November 7, 2000
INVENTOR(S) : Montse Llinas-Brunet, Murray D. Bailey, Teddy Halmos, Marc-Andre Poupart and Youla Tsantrizos It is certified that error appears in the above-identified patent and that said Letters Patent is hereby corrected as shown below:

Column 8,
Line 14, change "optioonally conctaing" to -- optionally containing --

Column 26,
Line 66, change "phophono" to -- phosphono --

Column 42,
Line 28, change "codled" to -- cooled --

Column 61, claim 1,
Line 66, change "thc" to -- the --

Column 63, claim 2,
Line 50, delete "according to claim 1, wherein" and insert

--

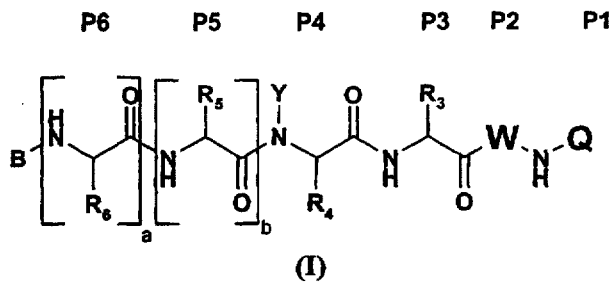

(I)

wherein B is an acyl derivative of formula $R_{11}$-C(O)- wherein $R_{11}$ is $C_{1-10}$ alkyl optionally substituted with carboxyl; or $R_{11}$ is $C_6$ or $C_{10}$ aryl or $C_{7-16}$ aralkyl optionally substituted with a $C_{1-6}$ alkyl;
a is 0 or 1;
$R_6$, when present, is the side chain of Asp or Glu;
b is 0 or 1;
$R_5$, when present, is the side chain of D-Asp, D-Val, or D-Glu;
Y is H or $C_{1-6}$ alkyl;
$R_4$ is $C_{1-10}$ alkyl or $C_{3-10}$ cycloalkyl;
$R_3$ is $C_{1-10}$ alkyl or $C_{3-10}$ cycloalkyl;

UNITED STATES PATENT AND TRADEMARK OFFICE
CERTIFICATE OF CORRECTION

PATENT NO. : 6,143,715
DATED : November 7, 2000
INVENTOR(S) : Montse Llinas-Brunet, Murray D. Bailey, Teddy Halmos, Marc-Andre Poupart and Youla Tsantrizos It is certified that error appears in the above-identified patent and that said Letters Patent is hereby corrected as shown below:

W is a group of formula II':

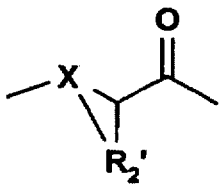

Formula II' wherein X is N; and
$R_2'$ is the side chain of proline and is substituted with $R_{17}$ at the 4-position with the stereochemistry shown in formula III':

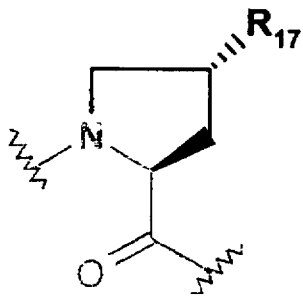

Formula III' wherein $R_{17}$ is $C_6$ or $C_{10}$ aryl, $C_{7-16}$ aralkyl, S-$C_6$ or $C_{10}$ aryl or S-$C_{7-16}$ aralkyl, each optionally substituted with $C_{1-6}$ alkyl, $NH_2$, OH, SH, halo, carboxyl or carboxy(lower)alkyl, said aryl or aralkyl optionally containing at least one heteroatom selected independently from the group consisting of: O, S, and N; and said aryl and aralkyl optionally fused with a second 5-, 6- or 7-membered ring to form a cyclic system or heterocycle, said second ring being optionally substituted with $NH_2$, OH, SH, halo, carboxyl or carboxy(lower)alkyl, and said second ring optionally containing at least one heteroatom selected independently from the group consisting of: O, S, and N;

UNITED STATES PATENT AND TRADEMARK OFFICE
CERTIFICATE OF CORRECTION

PATENT NO. : 6,143,715
DATED : November 7, 2000
INVENTOR(S) : Montse Llinas-Brunet, Murray D. Bailey, Teddy Halmos, Marc-Andre Poupart and Youla Tsantrizos It is certified that error appears in the above-identified patent and that said Letters Patent is hereby corrected as shown below:

or $R_{17}$ is $OR_{12}$ wherein $R_{12}$ is a $C_6$ or $C_{10}$ aryl or $C_{7-16}$ aralkyl, said first aryl or aralkyl optionally substituted with $C_{1-6}$ alkyl, $C_{3-7}$ cycloalkyl, $NH_2$, OH, SH, halo, $C_{1-6}$ alkoxy, carboxyl, carboxy(lower)alkyl, or a second aryl or aralkyl; said first and second aryl or aralkyl optionally containing at least one heteroatom selected independently from the group consisting of: O, S, and N; --

Column 63, claim 2,
Line 64, delete "$NR_{14}R_{14}$'S-$R_{14}$" and insert -- $NR_{14}R_{14}$'; S-$R_{14}$ --

Signed and Sealed this

Sixteenth Day of April, 2002

JAMES E. ROGAN
*Director of the United States Patent and Trademark Office*

*Attest:*

*Attesting Officer*